(12) United States Patent
Nan et al.

(10) Patent No.: US 7,741,348 B2
(45) Date of Patent: Jun. 22, 2010

(54) BISHETEROCYCLE TANDEM COMPOUNDS USEFUL AS ANTIVIRAL AGENTS, THE USES THEREOF AND THE COMPOSITIONS COMPRISING SUCH COMPOUNDS

(75) Inventors: Fajun Nan, Shanghai (CN); Jianping Zuo, Shanghai (CN); Wenlong Wang, Shanghai (CN); Guifeng Wang, Shanghai (CN); Haijun Chen, Shanghai (CN); Peilan He, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 115 days.

(21) Appl. No.: 11/886,593

(22) PCT Filed: Jan. 24, 2006

(86) PCT No.: PCT/CN2006/000124

§ 371 (c)(1),
(2), (4) Date: Nov. 5, 2007

(87) PCT Pub. No.: WO2006/097030

PCT Pub. Date: Sep. 21, 2006

(65) Prior Publication Data

US 2008/0306121 A1 Dec. 11, 2008

(30) Foreign Application Priority Data

Mar. 18, 2005 (CN) .......................... 2005 1 0024468

(51) Int. Cl.
*A61K 31/427* (2006.01)
*C07D 277/20* (2006.01)
(52) U.S. Cl. ....................... 514/365; 548/202; 548/203; 548/204
(58) Field of Classification Search ................. 514/365; 548/146, 200, 201, 202
See application file for complete search history.

(56) References Cited

FOREIGN PATENT DOCUMENTS

| WO | 98/31687 | 7/1998 |
|---|---|---|
| WO | WO 00/56724 | 3/2000 |
| WO | 00/56724 | 9/2000 |

OTHER PUBLICATIONS

Cited ref_STN_11886593_preliminary_04282009.*
Woodburn et al., Journal of Organic Chemistry (1954), 19, p. 863-867.*
Cao et al., Synthetic Metals (2005), 148(3), p. 219-226.*
STN-11886593B-core structure-08122009.*
Chemische Berichte, 1963, vol. 96, p. 438-41.*

Kaiser et al. "X-ray structures and ab initio study of the conformational properties of novel oxazole and thiazole containing di- and tripeptide mimetics" J. Chem. Soc. Perkin Trans. 2:1081-1085 (2000).
Li et al. "Synthesis of a directly connected thiazole-oxazole ring system present in microcin B17" J. Org. Chem. 61:778-780 (1996).
Videnov et al. "Synthesis of naturally occurring, conformationally restricted oxazaole and thiazole containing di- and tripeptide mimetics" Angewandte Chemie, International Ed. in English 35:1503-1506 (1996).
Kaiser et al., "X-Ray structures and ab initio study of the conformational properties of novel oxazole and thiazole containing di- and tripeptide mimetics," J. Chem. Soc., Perkin Trans. 2 (2000), (5), 1081-1085, compound 8.
Videnov et al., "Synthesis of naturally occurring, conformationally restricted oxazole- and thiazole-containing di- and tripeptide mimetics," Angewandte Chemie, International Edition in English (1996), 35 (13/14), 1503-1506, compounds 16-17.
Li et al., "Synthesis of a Directly Connected Thiazole-Oxazole Ring System Present in Microcin B17," Journal of Organic Chemistry (1996), 61(2), 778-80, compound 8.
Wang et al., "First total synthesis of Leucamide A," Journ. of organic chemistry 68 (4): 1636-1639, Feb. 21, 2003, compounds 4, 8 and 9.
Wang et al., "Synthesis and biological evaluation of novel bisheterocycle-containing compounds as potential anti-influenza virus agents," Bioorganic & Medicinal Chemistry Letters, Dec. 1, 2005, 15(23), 5284-5287, the whole document.
International Search Report for PCT/CN2006/000124 mailed May 18, 2006.
International Search Report; PCT/CN2006/000124; 7 pages.
"Synthesis of Naturally Occurring, Conformationally Restricted oxazole- and thiazole-containing di- and tripeptide Mimetics"; Videnov, Georgi et al.; Angewandte Chemie, International Edition in English (1996), 35 (13/414), 1503-1506, pp. 1503-1506.
"X-Ray structures and ab initio study of the conformational properties of novel oxazole and thiazole containing di- and tripeptide mimetics"; Kaiser, Dietmar et al.; J. Chem. So., Perkin Trans. 2 (2000), pp. 1081-1085.
"Synthesis of a Directly Connected Thiazole-Oxazole Ring System Present in Microcin B17"; Li, Gang et al.; J. Org. Che., 1996, 61, pp. 778-780.

(Continued)

*Primary Examiner*—Yong Chu
(74) *Attorney, Agent, or Firm*—Nixon & Vanderhye, P.C.

(57) ABSTRACT

The present invention provides small molecule compounds of bisheterocycle in tandem having the structural formula of P1-P2, and the use thereof as well as a composition containing the compounds, each of P1 and P2 is an unsaturated 5-member heterocyclic ring having one or two heteroatoms. This compound may effectively inhibit the replication of influenza virus, the DNA replication of hepatitis B virus (HBV), and the formation of HBsAg and HBeAg. These compounds can be used for the preparation of a medicament for viral diseases, and may overcome the limitations of the known nucleosides drugs, including cytotoxicity, the requirement of other drugs having different structures for against the drug-resistant virus variants induced by long-term therapy. The structure of the compounds according to the invention is relatively simple and easy to be prepared.

4 Claims, No Drawings

OTHER PUBLICATIONS

"First Total Synthesis of Leucamide A"; Wang Wenlong et al.; J. Org. Chem., 2003, 68, pp. 1636-1639.

"Synthesis and biological evaluation of novel bisheterocycle-containing compounds as potential anti-influenza virus agents"; Wang Wen-Long et al.; Bioorganic & Medicinal Chemistry Letters 2005; pp. 5284-5287.

* cited by examiner

BISHETEROCYCLE TANDEM COMPOUNDS USEFUL AS ANTIVIRAL AGENTS, THE USES THEREOF AND THE COMPOSITIONS COMPRISING SUCH COMPOUNDS This application is the U.S. national phase of International Application No. PCT/CN2006/000124, filed 24 Jan. 2006 which designated the U.S. and claims priority to Chinese Patent Application No. 200510024468.5, filed 18 Mar. 2005, the entire contents of each of which are hereby incorporated by reference.

TECHNICAL FIELD

The present invention relates to a kind of anti-viral inhibitors, particularly to a kind small molecule organic compounds of bisheterocycle in tandem which may be used as non-nucleoside antiviral inhibitors. The compounds can be used as the drugs for the treatment of diseases such as influenza, hepatitis B, herpes and acquired immunodeficiency syndrome and the like. The present invention also relates to the use of the compounds and the compositions containing the same compounds.

BACKGROUND ART

Human pathogenic viruses are a kind of nucleic acid particles with very simple structure. Most of them lack of enzymatic system, and they have to depend on the host cells to replicate their nucleic acids and proteins and then assemble into virus particles so that the viruses are replicated. Virus infection can cause various diseases and threaten the human health and lives severely. At present, the viruses with high morbidity and great harmfulness mainly include influenza virus, hepatitis B virus, AIDS virus, cytomegalovirus and herpes virus, etc.

Now in the treatment of viral diseases, there still lack of drugs of high specificity, and the common drugs used in clinical mainly are divided into the following types: the antiviral drugs for inhibiting the virus replication; the immunomodulators for enhancing the body's immune function; the antitussive, anodyne, antipyretic and antipyrotic drugs and the like against clinical symptom; the anti-infection drugs for preventing secondary infection; the vaccines for preventing virus infection and the disinfectants for blocking the transmission of viruses, etc.

At present, the study of new drugs for treatment of viral diseases is highlighted on the antiviral drugs. The widely used anti-influenza virus drugs include the adamantanamine drugs, the neuramidinase inhibitors of influenza virus, the receptor blocking agent of influenza virus and the antisense oligonucleotide against influenza virus etc. And the ones used clinically mainly are the adamantanamine drugs and the neuramidinase inhibitors. However, the hepatitis virus infection is recognized as an international therapeutic problem so far.

In 1980's, the vidarabine, vidarabine phosphate, acyclovir, zidovudine have been studied. However, they are not used to treat hepatitis now due to their poor therapeutic effect and strong toxic reaction. In recent years, many nucleoside drugs, such as lamivudine, famciclovir, lobucavir, adefovir dipivoxiil, FTC (dideoxyfluorinethiocytosine), FMAU (fluoromethylarabinosyluracil), FDDC (fluoro-dideoxycytosine), BMS 200475 (epoxyhydroxylcarbodeoxy guanosine), have been developed by screening the drugs against hepatitis B virus and hepatitis C virus with the established hepatoma carcinoma cell lines, hepatitis virus transfected cell lines or transgenic cell lines, and transgenic mouse hepatitis animal model, they have obvious inhibiting activities to HBV. More than 30 kinds of drugs were carried out the preclinical trial research by the researchers in 1998-2002. And there are 21 drugs entering the stage II-III clinical trial recently. Among these trial drugs, the ones for anti hepatitis B virus are mostly the anti HIV revertase inhibitors and anti-herpes virus DNA polymerase inhibitors. Among other things, enticavir have entered stage III clinical trial, and may go on the market soon. The trial drugs for anti hepatitis C virus are mostly the broad spectrum antiviral drugs or RNA virus inhibitors, and the immunomodulators having antiviral activity.

At present, most of the approved antiviral drugs are nucleoside compounds. In the course of clinical uses, they have been found to have the following disadvantages: 1) cytotoxicity; 2) occurrence of drug resistant virus variants induced by long-term medication to which other drugs having different structure are need. Therefore, the non-nucleoside antiviral drugs became an aspect catching much attention.

DISCLOSURE OF THE INVENTION

An object of the present invention is to provide small molecule organic compounds of bisheterocycle in tandem used as a non-nucleoside antivirus inhibitor.

Another object of the present invention is to provide medical compositions containing the above compounds.

An additional object of the present invention is to provide a medical use of the above compounds.

According to the aspect of the present invention, the present invention provides the compounds having a structure represented by the following structural formula I:

$$P1\text{-}P2 \qquad\qquad I$$

wherein,

Each of P1 and P2 is an unsaturated 5-member heterocyclic ring, and each of the unsaturated 5-member heterocyclic rings P1 and P2 contains one or two heteroatoms selected from the group consisting of N, O or S, and/or each of the unsaturated 5-member heterocyclic rings P1 and P2 is optionally substituted by one or two substitute groups R, and The said substitute group R is hydrogen; halogen atoms; phenyl or halophenyl; benzyl; C1-C13 alkyl substituted by halogen atom, C1-C6 alkoxyl or hydroxyl; thiazolyl, C2-C6 alkenyl; C3-C6 cycloalkyl; C1-C6 alkyl, C2-C6 alkenyl, phenyl and benzyl substituted by oxygen; C1-C2 alkoxycarbonyl; carboxyl; carbamoyl having the structure formulae

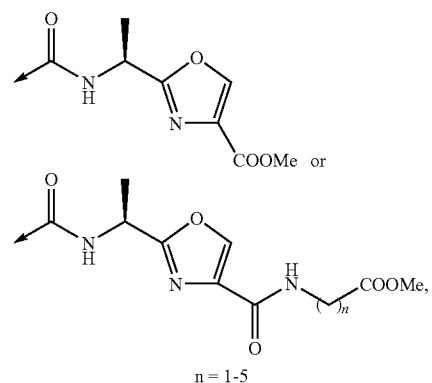

n = 1-5 wherein n=1 to 5; acetyl substituted by nitrile group; substituted aminoalkyl having the structure of

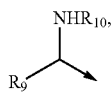

wherein,

R$_9$ is hydrogen, isopropyl or benzyl, and

R$_{10}$ is hydrogen; C2-C8 alkenylacyl; C2-C6 alkanoyl; C1-C6 alkanoyl substituted by alkoxyl; C3-C6 cycloalkanoyl; benzoyl unsubstituted or optionally substituted by one, two or three groups selected from C1-C6 alkoxyl, C1-C6 alkylamino, halogen atom and hydroxyl; benzylacyl; thienyl formacyl; pyridyl formacyl; acylamino; tert-butoxy carbonyl; 2-bromo-thiazolyl-4-formacyl having the structure of

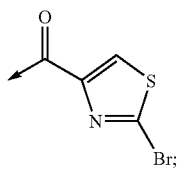

2,5-dibromo-thiazolyl-4-formacyl having the structure of

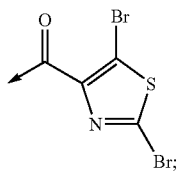

2-methyl-thiazolyl-4-formacyl having the structure of

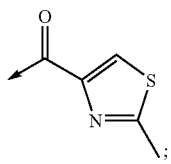

pyridyl formacyl substituted by 3-tert-butoxylcarbonylamino having the structure of

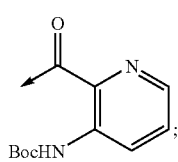

2-substituted alkylamino-4-thiazolyl formacyl having the structure of

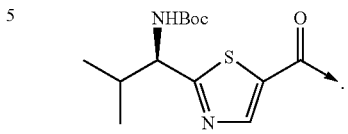

The compound according to the present invention is represented by the following structural formula II:

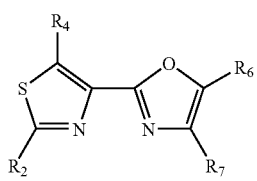

II wherein,

R$_2$ is hydrogen or alkyl substituted by a substituted amino having the structure of

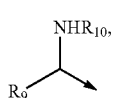

wherein R$_9$ and R$_{10}$ have the same definition as above;

R$_4$ is hydrogen, C1-C6 alkyl or benzyl;

R$_6$ is hydrogen or C1-C6 alkyl; and

R$_7$ is carboxyl, C1-C2 alkoxycarbonyl, carbamoyl having the structure of

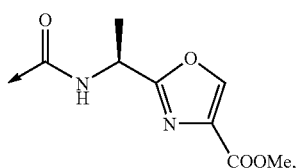

or carbamoyl having the structure of

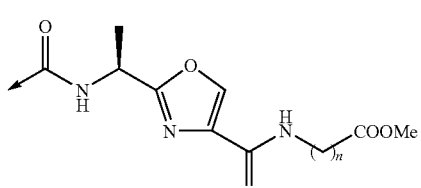

wherein n=1 to 5.

More preferably, the compound according to the present invention has the structure represented by formula III,

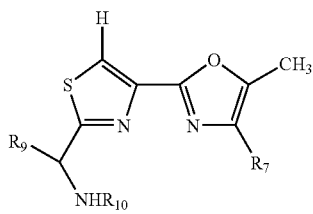

wherein,
$R_7$ is carboxyl,
$R_9$ is isopropyl or hydrogen,
$R_{10}$ is cyclopentyl formacyl, o-methoxyl benzoyl, cyclopentyl-1-ene-acetyl having the structure of

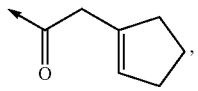

o-fluoro benzoyl or thienyl formacyl;
or
$R_7$ is methoxylcarbonyl,
$R_9$ is isopropyl, benzyl or hydrogen,
$R_{10}$ is hydrogen; C2-C8 alkenylacyl; C2-C6 alkanoyl; acetyl substituted by benzyloxy; C3-C6 cycloalkanoyl; benzoyl unsubstituted or optionally substituted by one, two or three groups selected from methoxyl, fluorine atom, amino or hydroxyl; benzylacyl; thienyl formacyl; pyridyl formacyl; pyridyl formacyl substituted by 3-tert-butoxylcarbonylamino having the structure of

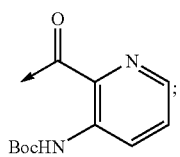

2-substituted alkylamino-4-thiazolyl formacyl having the structure of

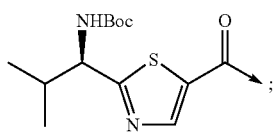

2-bromo-thiazolyl-4-formacyl having the structure of

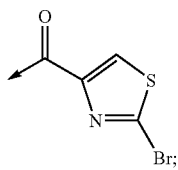

2,5-dibromo-thiazolyl-4-formacyl having the structure of

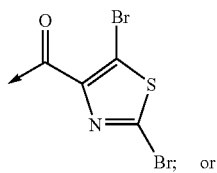

2-methyl-thiazolyl-4-formacyl having the structure of (structure)

or,
$R_7$ is carbamoyl having the structure of

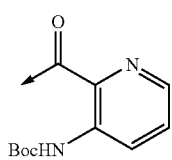

$R_9$ is isopropyl,
$R_{10}$ is hydrogen, acetyl substituted by benzyloxy, benzoyl unsubstituted or optionally substituted by single fluorine atom, benzylacyl, pyridyl formacyl, pyridyl formacyl substituted by 3-tert-butoxylcarbonyl amino having the structure of (structure)

or 2-substituted alkylamino-4-thiazolyl formacyl having the structure of

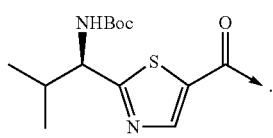

Particularly, the compound according to the present invention has the structure represented by the following formula IV:

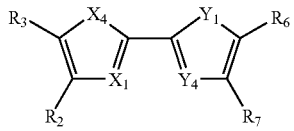

wherein, $R_2$, $R_3$, $R_6$ and $R_7$ are independently hydrogen; halogen atoms; phenyl or halophenyl; benzyl; C1-C13 alkyl substituted by halogen atoms, C1-C6 alkoxyl or hydroxyl; C2-C6 alkenyl; C3-C6 cycloalkyl; C1-C6 alkyl, C2-C6 alkenyl, phenyl or benzyl substituted by oxygen atom; amido; C1-C2 alkoxycarbonyl; or carboxyl;

$X_4$ is O, S, NH or N;
$X_1$ is N, NH or $CH_2$;
$Y_1$ is O, S or NH; and
$Y_4$ is N or $CH_2$.

Furthermore, for the above-mentioned compound, when $R_2$ is H and $Y_4$ is N, $R_3$ is C1-C6 alkyl;
$R_6$ is C1-C13 alkyl; phenyl or halophenyl; benzyl; substituted alkyl containing halogen atoms, alkoxyl or hydroxyl; C2-C6 alkenyl; C3-C6 cycloalkyl; or halogen atoms;
$R_7$ is hydrogen; phenyl or halophenyl; benzyl; C1-C13 alkyl; C1-C13 alkyl substituted by halogen atoms, C1-C6 alkoxy or hydroxyl; C2-C6 alkenyl; C3-C6 cycloalkyl; C1-C6 alkyl substituted by oxygen; C1-C2 alkoxycarbonyl; or carboxyl;
$X_4$ is O, S or NH;
$X_1$ is N or $CH_2$; and
$Y_1$ is O, S or NH.

And, for the above compound, when $R_3$ is H, $R_2$ is H and $Y_4$ is N, $R_6$ is C1-C13 alkyl, phenyl or halophenyl, benzyl, C1-C6 alkyl substituted by alkoxyl, C2-C6 alkenyl, C3-C6 cycloalkyl or halogen atoms;
$R_7$ is hydrogen, phenyl or halophenyl, benzyl, C1-C13 alkyl, C1-C6 alkyl substituted by alkoxyl, C2-C6 alkenyl, C3-C6 cycloalkyl, C1-C2 alkoxycarbonyl or carboxyl;
$X_4$ is O, S or NH;
$X_1$ is N or $CH_2$; and
$Y_1$ is O, S or NH.

In another aspect of the present invention, the compound according to the present invention may have the structure represented by the formula V:

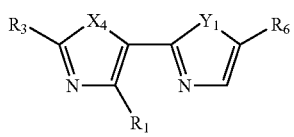

wherein, $R_1$ is benzyl, C1-C6 alkyl or C2-C6 alkenyl;
$R_6$ is C1-C6 alkoxyl;
$R_3$ is thiazolyl, thienyl, phenyl, benzyl, C1-C6 alkyl, C2-C6 alkenyl or C3-C6 cycloalkyl;
$X_4$ is O or S; and
$Y_1$ is O or S.

The compound according to the present invention can be prepared by the following processes:

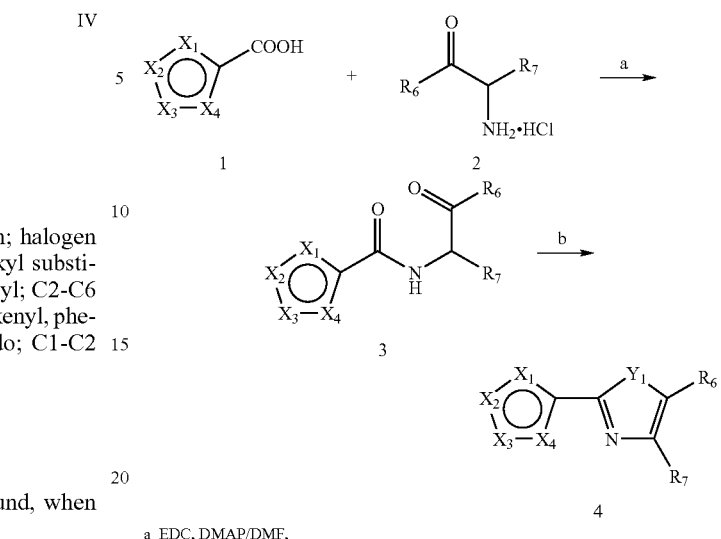

a EDC, DMAP/DMF,
b $NH_4OAc$, NaOAc or Lawesson's reagent or $POCl_3$

1) Compound 3 is obtained by condensation reaction between Compound 1 and Compound 2;

2) Compound 4 is obtained by cyclizing Compound 3.

Wherein, $R_6$ and $R_7$ are independently phenyl or halophenyl; benzyl; C1-C13 alkyl substituted by halogen atoms, C1-C6 alkoxyl or hydroxyl; C2-C6 alkenyl; C3-C6 cycloalkyl; C1-C6 alkyl, C2-C6 alkenyl, phenyl or benzyl substituted by oxygen; amido; C1-C2 alkoxycarbonyl; or carboxyl;

$X_1$ is N, NH, O, S or $CR_1$;
$X_2$ is N, NH, O, S or $CR_2$;
$X_3$ is N, NH, O, S or $CR_3$;
$X_4$ is N, NH, O, S or $CR_4$;
$Y_1$ is O, S or NH;
$R_1$, $R_2$, $R_3$ and $R_4$ have the same definition as described above.

The structure of Lawesson's reagent is

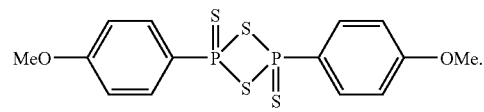

In particular, the preferred compound according to the present invention may be prepared by the following chemical reactions.

Compound 7 is prepared according to the following chemical reaction:

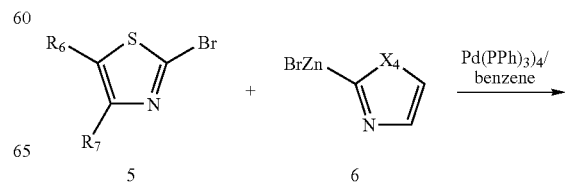

-continued

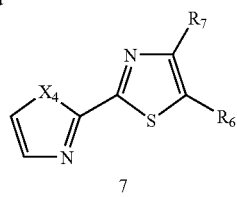

R₆ and R₇ are independently phenyl or halophenyl; benzyl; C1-C13 alkyl substituted by halogen atoms, C1-C6 alkoxyl or hydroxyl; C2-C6 alkenyl; C3-C6 cycloalkyl; C1-C6 alkyl, C2-C6 alkenyl, phenyl or benzyl substituted by oxygen; amido; C1-C2 alkoxycarbonyl; or carboxyl; and X₄ is O or S.

Compound 11 is prepared according to the following chemical reactions:

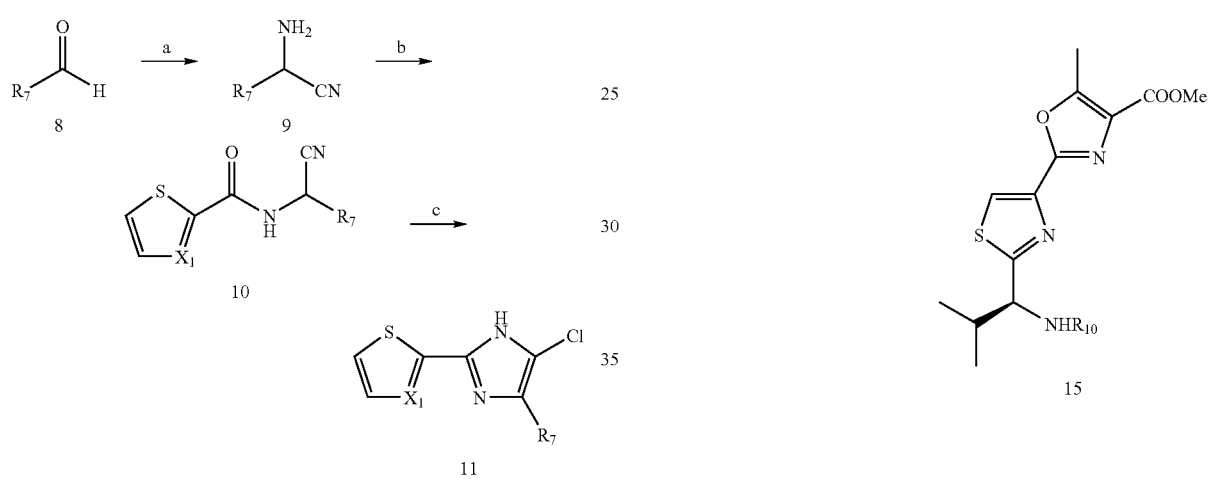

a 25% NH₄OH, KCN, NH₄Cl;
b EDC, DMAP, DMF, Thiazole-2-carboxylic acid or Thiophene-2-carboxylic acid
c PPh₃, CCl₄, CH₃CN Wherein, R₇ is phenyl, benzyl or n-butyl; and X₁ is N or CH₂.

Compound 13 is prepared according to the following chemical reaction:

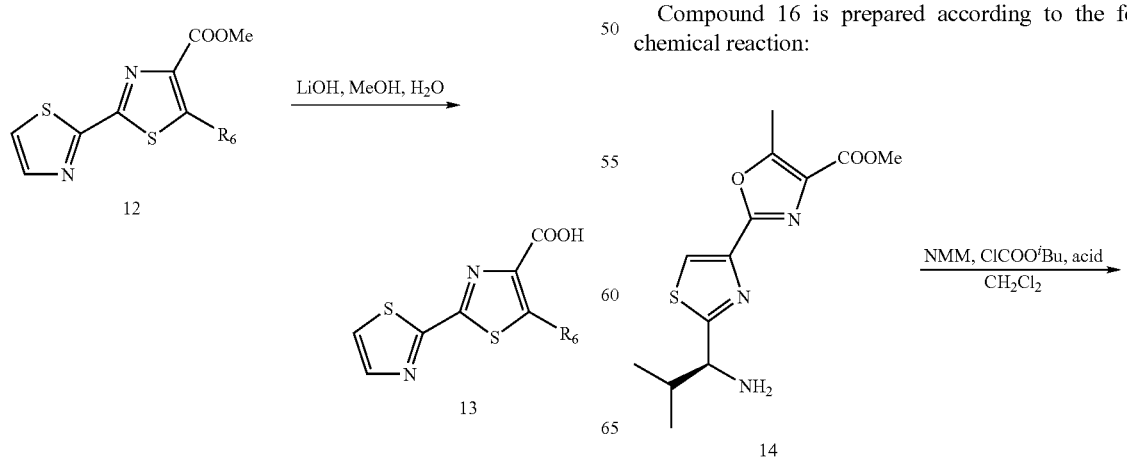

Wherein, R₆ is H, isobutyl, benzyl or n-butyl.

Compound 15 is prepared according to the following chemical reaction:

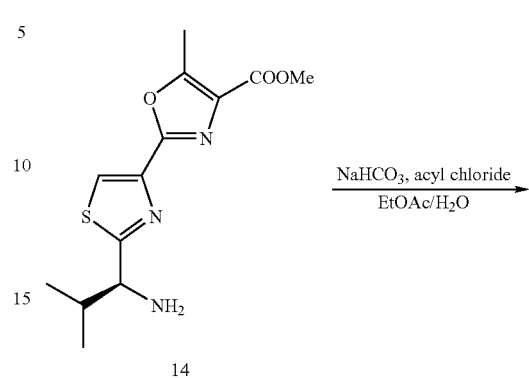

Wherein, R₁₀ is C2-C8 alkenlyacyl; C2-C6 alkanoyl; acetyl substituted by benzyloxy; C3-C6 cycloalkanoyl; benzoyl unsubstituted or optionally substituted by one, two or three groups selected from methoxyl, fluorine atom or hydroxyl; benzylacyl; or formacyl.

Compound 16 is prepared according to the following chemical reaction:

-continued

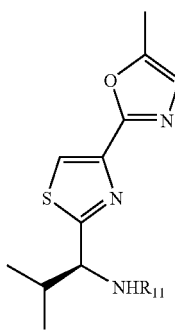

16

Wherein, R₁₁ is C2-C8 alkenlyacyl.

Compound 17 is prepared according to the following chemical reaction:

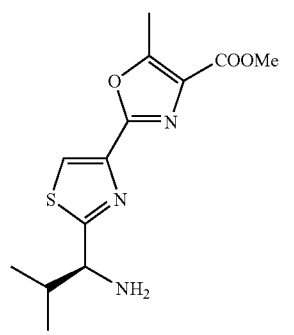

14

→ EDCI, HOBT, molecular sieve, acid / DMF →

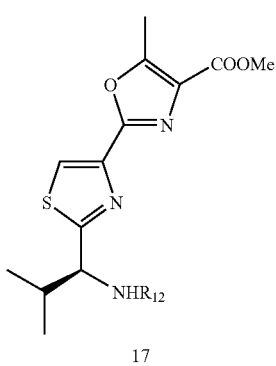

17

Wherein, R₁₂ is pyridyl formacyl, pyridyl formacyl substituted by 3-tert-butoxylcarbonyl amino

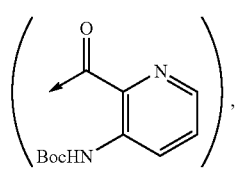

2-substituted alkylamino-4-thiazolyl formacyl

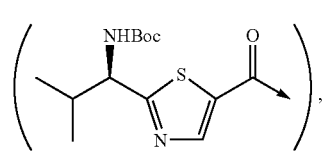

2-bromo-thiazolyl-4-formacyl

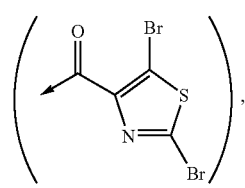

2,5-dibromo-thiazolyl-4-formacyl

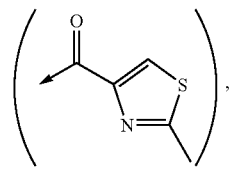

2-methyl-thiazolyl-4-formacyl

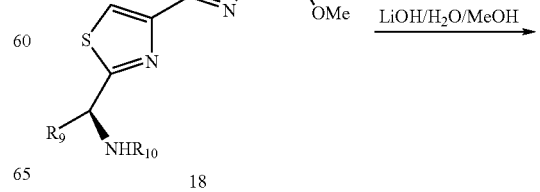

pyridyl formacyl, o-amino benzoyl, o-methoxyl benzoyl, o-hydroxy benzoyl, or thienyl formacyl.

Compound 19 is prepared according to the following chemical reaction:

18

→ LiOH/H₂O/MeOH →

-continued

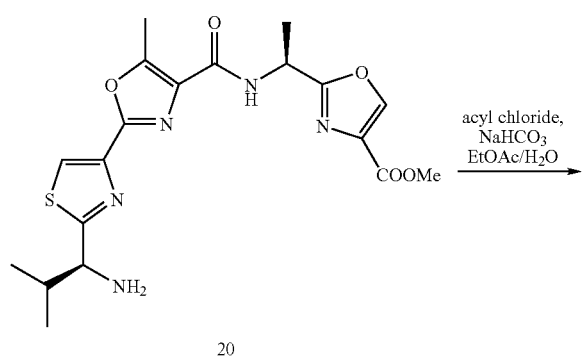

19

Wherein, $R_{10}$ is cyclopentyl formacyl, o-methoxyl benzoyl, cyclopentyl-1-ene-acetyl, thienyl formacyl, o-fluoro benzoyl; and $R_9$ is benzyl or isobutyl.

Compound 21 is prepared according to the following chemical reaction:

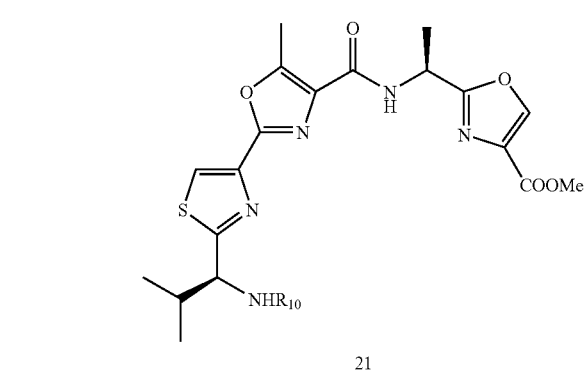

21

Wherein, $R_{10}$ is C2-C8 alkenlyacyl, C2-C6 alkanoyl, acetyl substituted by benzyloxy, C3-C6 cycloalkanoyl, benzoylunsubstituted or optionally substituted by single fluorine atom, benzylacyl or formacyl.

Compound 22 is prepared according to the following chemical reaction:

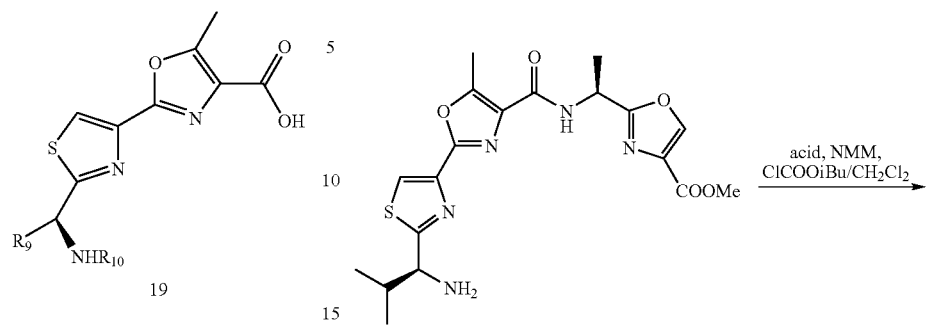

20

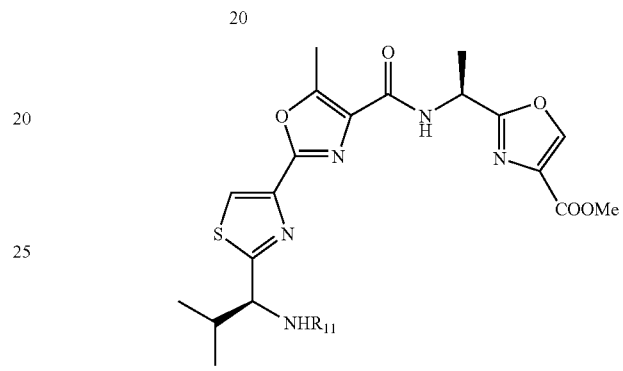

22

Wherein, $R_{11}$ is C2-C8 alkenlyacyl.

Compound 23 is prepared according to the following chemical reaction:

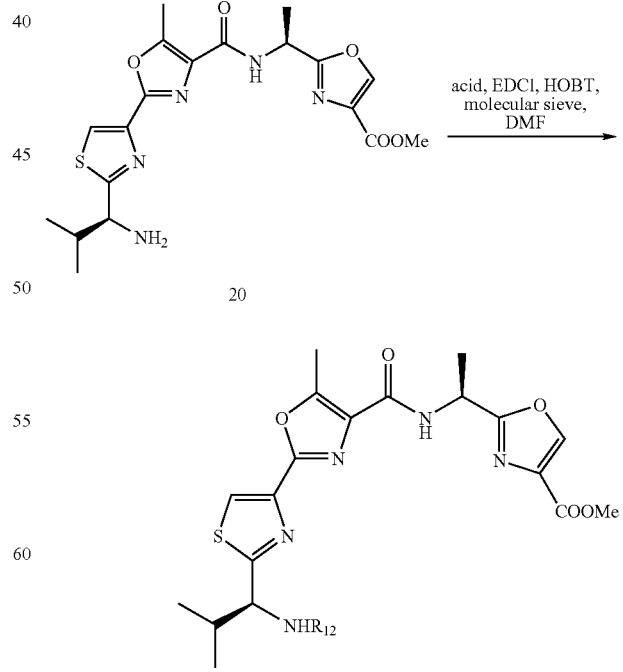

23

Wherein, $R_{12}$ is pyridyl formacyl, pyridyl formacyl substituted by 3-tert-butoxylcarbonyl amino

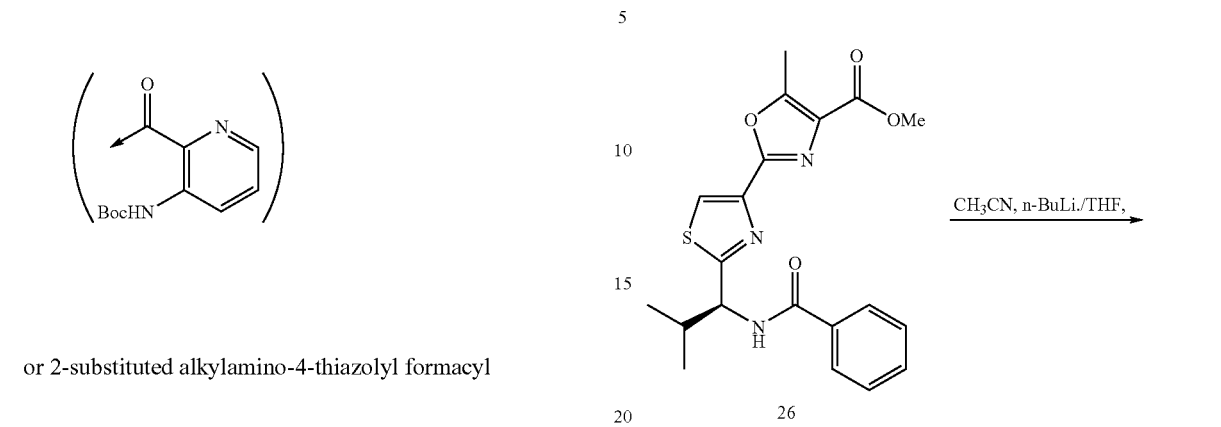

or 2-substituted alkylamino-4-thiazolyl formacyl

Compound 25 is prepared according to the following chemical reaction:

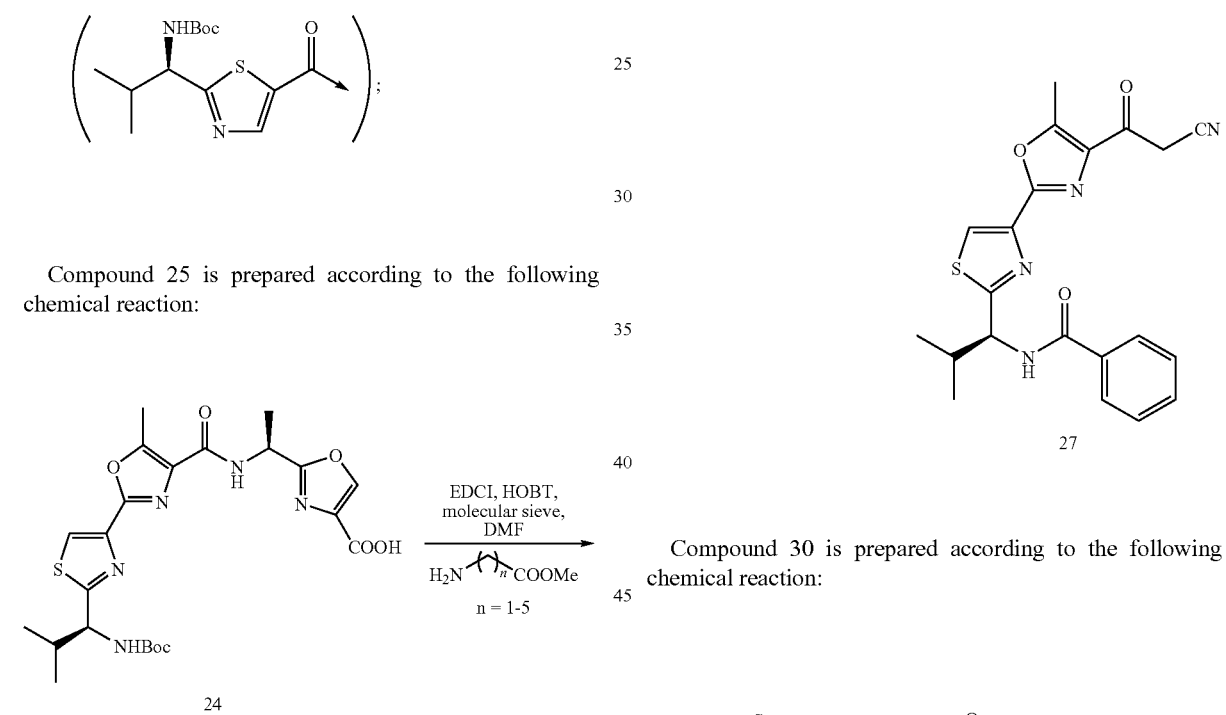

Compound 27 is prepared according to the following chemical reaction:

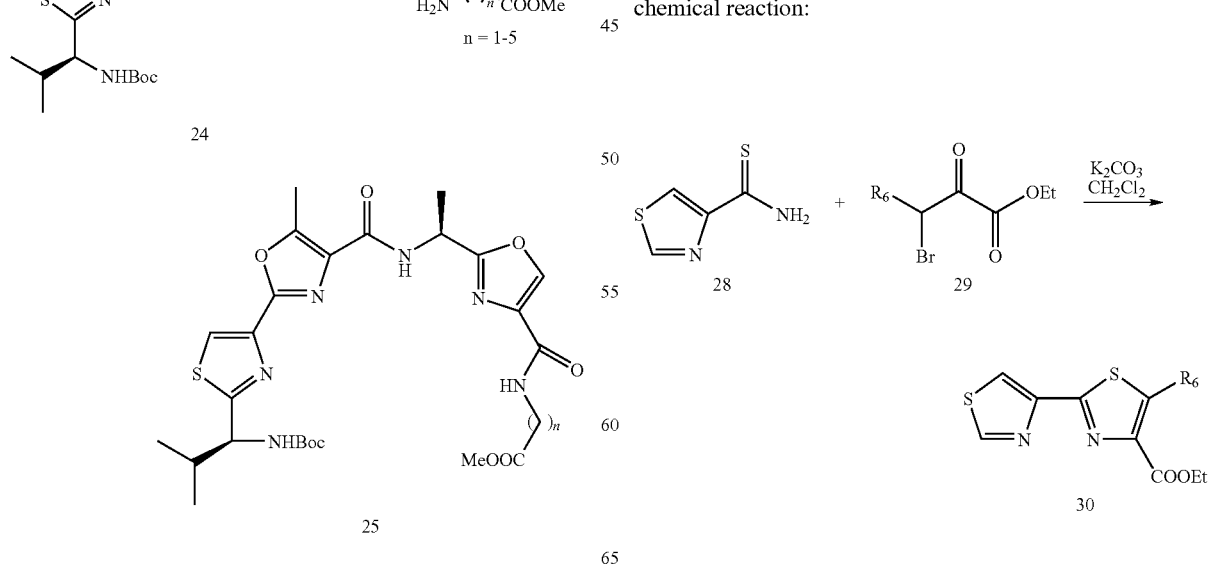

Compound 30 is prepared according to the following chemical reaction:

Wherein, $R_6$ is H or methyl.

Compound 36 is prepared according to the following chemical reactions:

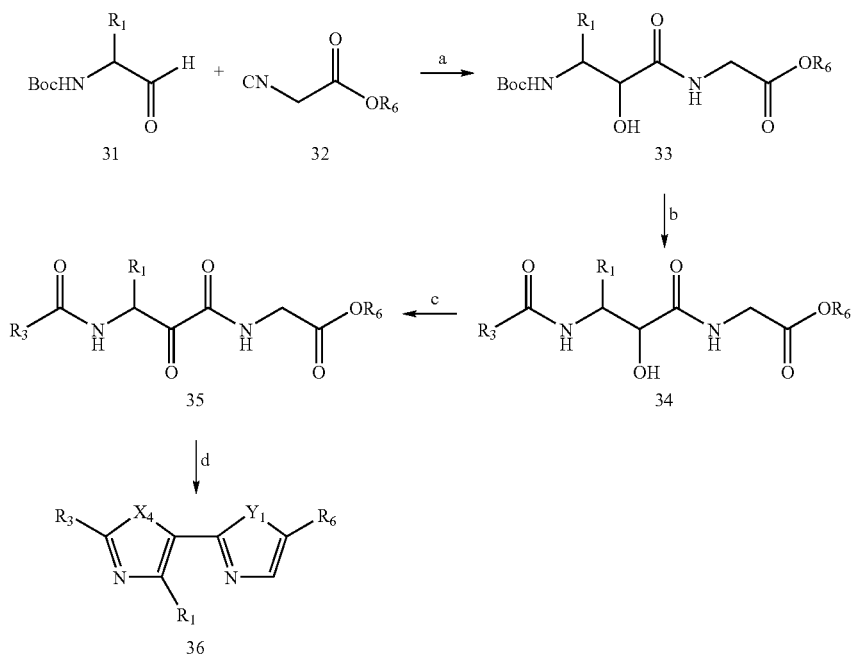

a TFA (trifluoroacetic acid), pyridine, CH$_2$Cl$_2$;
b THF, EDCI, DMAP, DMF;
c IBX having the structure of

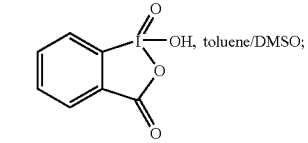

, toluene/DMSO;

d POCl$_3$ wherein, $R_6$ is C1-C2 alkoxy; $R_3$ is thiazolyl, thienyl, phenyl, benzyl, C1-C6 alkyl, C2-C6 alkenyl or C3-C6 cycloalkyl; $R_1$ is benzyl, C1-C6 alkyl or C2-C6 alkenyl; $X_4$ is O or S; and $Y_1$ is O or S.

Compound 38 is prepared according to the following chemical reaction:

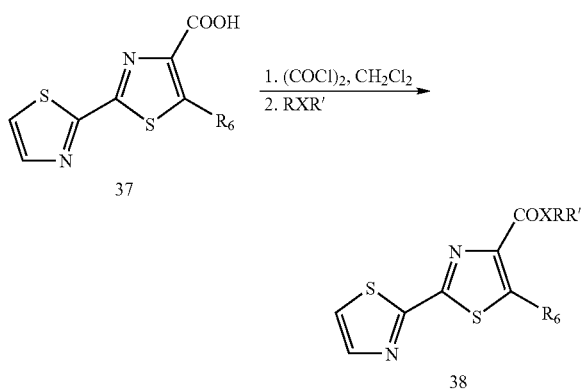

Wherein, $R_6$ is isobutyl; R and R' are independently phenyl, benzyl, H or C1-C6 alkyl; and X is N or O.

The above reactions may be carried out in a solvent such as N,N-dimethyl formamide (DMF), acetonitrile (CH$_3$CN), methanol, dichloromethane, tetrahydrofuran (THF), dichloroethane, toluene, benzene, dioxane, water or a mixture thereof. As the case may be, an activator, such as pyridine, N-methylmorpholine, isobutyl chloroformate, triethylamine, diisopropylethylamine, DMAP and the like, is necessary to be added into a certain reaction. The reaction temperature typically is −78° C.~140° C. according to the reaction situation of a specific compound (for example Compound Wang413.49 etc.). The reaction time is dependent on the specific reactants. The completion degree of the reaction typically is tracked and measured by TLC. After reaction, after-treatment methods generally used includes filtration, concentration of the reaction solution in order to remove the solvent, extraction and column chromatography separation etc. The final product is identified by NMR.

The methods for synthesizing a small molecule organic compound of bisheterocycle in tandem in the present invention may be found in the following literature: 1. *J. Org. Chem.* 1973; 38; 3571. 2. WO9831687, 1997. 3. *Org. Process Res. Dev.* 2003; 7; 696. 4. *Org. Lett.* 2004; 6; 929. 5. *Chem. Pharm. Bull.* 1983; 31; 4549. 6. *J. Org. Chem.* 2003; 68; 1636. 7. *Org. Lett.* 2000; 2; 2769 etc.

The present invention also provides a medical composition containing the above compound as an active component, and this composition can also contain conventional pharmaceutic adjuvant.

According to the aspect of the present invention, the compound of the present invention may be used as an antivirus inhibitor.

The compound according to the present invention may be used to prepare the medicament for viral diseases.

Furthermore, the compound according to the present invention and the composition comprising such compound may be used to treat the viral diseases caused by influenza virus, hepatitis virus, herpes virus or AIDS virus.

The present invention provides a small molecular organic compound of bisheterocycle in tandem used as a non-nucleoside antivirus inhibitor. This compound may effectively inhibit the replication of influenza virus, the DNA replication of hepatitis B virus (HBV), and the formation of HBsAg and HBeAg. This compound can be used for the preparation of a medicament for viral diseases, and may overcome the limitations of the known nucleosides drugs, including cytotoxicity, the requirement of other drugs having different structure for against the drug-resistant virus variants induced by long-term therapy. The structure of the compound according to the invention is relatively simple and easy to be prepared.

BEST MODE FOR CARRYING OUT THE INVENTION

Preparation Examples

The present invention is further illustrated with reference to the following specific examples which, however, do not limit the present invention.

In the following preparation examples, NMR was measured using Mercury-Vx 300M produced by Varian, and the NMR scaling is: δ H/C 7.26/77.0 ppm ($CDCl_3$). The reagents were mainly provided by Shanghai Chemical Reagent Co., Ltd. The purification of the products were performed mainly with column chromatography of silica gel (200-300 mesh). And the type of the silica gel used in column chromatography was coarse hollow (ZLX-II), and it is produced by the Branch of Qingdao Haiyang Chemical Plant.

Example 1

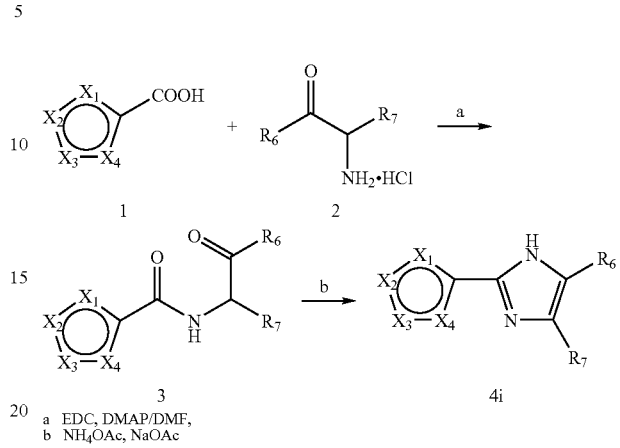

a EDC, DMAP/DMF,
b $NH_4OAc$, NaOAc

Compound 1 (3 mmol), compound 2 (3 mmol), N-ethyl-N'-(3-dimethylaminopropyl)carbodiimide hydrochloride (EDC) (3.3 mmol) and N,N-dimethylpyridine (DMAP) (0.3 mmol) were mixed with a molecular sieve, and the resulted mixture was cooled in ice bath (0° C.). Then DMF and pyridine (4.5 mmol) were added in turn. The progress of reaction was tracked by TLC. After the reaction was completed, the reactant was diluted with water and extracted with EtOAc. The solvent was removed completely by concentration. Then compound 3 was obtained through column chromatograph (yield 60%). Subsequently, compound 3 (0.3 mmol) was mixed with ammonium acetate ($NH_4OAc$) (15 mmol) and sodium acetate (NaOAc) (30 mmol) and heated to 130° C., and the progress of reaction was tracked by TLC. Then the reactant was cooled to room temperature, and diluted with water, extracted with ethyl acetate. The solvent was removed completely by concentration. Then compound 4i (Wang279-1) was obtained by separation through column chromatograph with petroleum ether/ethyl acetate (volume ratio 1:1) (yield 31%). The following compounds were synthesized by the same method:

TABLE 1-1

| Compound | Structure formula | $^1$H NMR ($CDCl_3$, 300 MHz) data |
|---|---|---|
| Wang279-1 | | δ 0.86(d, 6H), 1.34(t, 3H), 1.94(m, 1H), 2.79(d, 2H), 4.33(q, 2H), 7.39(d, 1H), 7.78(d, 1H). |
| Wang278 | | δ 0.89(t, 3H), 1.28~1.45(m, 5H), 1.66(m, 2H), 2.94(t, 2H), 4.31(q, 2H), 7.01(dd, 1H), 7.30(d, 1H), 7.60(d, 1H). |
| Wang292 | | δ 0.87(t, 3H), 1.28~1.43(m, 7H), 1.67(m, 2H), 2.91(t, Hz, 2H), 4.35(q, 2H), 7.06(dd, 1H), 7.34 (d, 1H), 7.49(d, 1H). |

TABLE 1-1-continued

| Compound | Structure formula | $^1$H NMR (CDCl$_3$, 300 MHz) data |
|---|---|---|
| Wang264-1 | | δ 1.25-1.34(m, 9H), 3.69(m, 1H), 4.33(q, 2H), 7.03(dd, 1H), 7.30(d, 1H), 7.53(d, 1H). |
| Wang265-1 | | δ 1.26(d, 6H), 1.39(t, 3H), 3.87(m, 1H), 4.38(q, 2H), 7.37(d, 1H), 7.75(d, 1H). |
| Wang265 | | δ 0.98(t, 3H), 1.40(t, 3H), 1.75(m, 2H), 2.92(t, 2H), 4.39(q, 2H), 7.43(d, 1H), 7.84(d, 1H). |
| Wang223 | | δ 2.56(s, 3H), 3.88(s, 3H), 7.41(d, 1H), 7.80(d, 1H). |
| Wang222-1 | | δ 2.53(s, 3H), 3.80(s, 3H), 6.96(dd, 1H), 7.24(d, 1H), 7.58(d, 1H). |
| Wang278-1 | | δ 0.95(d, 6H), 1.35(t, 3H), 2.08(m, 1H), 2.83(br, 2H), 4.34(q, 2H), 7.26(d, 1H), 7.34(d, 1H), 7.57(m, 1H). |
| Wang404 | | δ 0.87(3H), 1.2-1.60(22H), 1.40-1.69(4H), 2.87(2H), 4.37(q, 2H), 7.09(m, 1H), 7.26(m, 1H), 7.46(m, 1H). |
| Wang276 | | δ 1.23(t, 3H), 2.39(dd, 2H), 3.02(t, 2H), 4.29(q, 2H), 4.91(d, 1H), 4.96(d, 1H), 5.74-5.85(m, 1H), 7.00(dd, 1H), 7.27(d, 1H), 7.57(d, 1H). |
| Wang350 | | δ 1.42(t, 3H), 4.22(q, 2H), 7.02(ddd, 1H), 7.10(dd, 1H), 7.18(dd, 1H), 7.40(dd, 1H), 7.45(dd, 1H), 7.64(d, 1H). |

TABLE 1-1-continued

| Compound | Structure formula | $^1$H NMR (CDCl$_3$, 300 MHz) data |
|---|---|---|
| Wang264 | | δ 0.95(t, 3H), 1.71(m, 2H), 2.87(m, 2H), 4.32 (q, 2H), 7.05(m, 1H), 7.30(m, 1H), 7.51(m, 1H). |
| Wang298 | | δ 1.19(t, 3H), 4.24(q, 2H), 7.01(m, 1H), 7.31 (5H), 7.58(d, 1H), 7.74(m, 1H). |
| C226 | | δ 7.04(dd, 1H), 7.22(m, 2H), 7.32(m, 3H), 7.46 (d, 1H), 7.68(m, 2H). |
| C262 | | δ 0.94~1.10(m, 4H), 1.38(t, 3H), 2.56(m, 1H), 4.38(q, 2H), 7.05(dd, 1H), 7.33(d, 1H), 7.49(d, 1H). |
| C263-1 | | δ 0.82~0.88(4H), 1.43(t, 3H), 2.57(m, 1H), 4.35 (q, 2H), 7.39(d, 1H), 7.84(d, 1H), 10.56(bs, NH). |
| C277 | | δ 1.38(t, 3H), 2.04(m, 2H), 2.37(m, 4H), 4.09 (m, 1H), 4.36(q, 2H), 7.41(d, 1H), 7.82(d, 1H). |
| C291 | | δ 1.40(t, 3H), 1.56~1.90(8H), 3.89(m, 1H), 4.39 (q, 2H), 7.36(d, 1H), 7.54(d, 1H), 11.06(bs, NH). |
| C324 | | δ 1.47(t, 3H), 4.44(q, 2H), 7.13(dd, 1H), 7.28~7.48(m, 3H), 7.55~7.60(m, 3H), 7.66(d, 1H), 9.77(bs, NH). |
| C311-2 | | δ 1.04(d, 6H), 1.44(t, 3H), 2.02(m, 1H), 2.94(d, 2H), 4.34(d, 2H), 7.11(s, 1H), 7.21(t, 1H), 7.26 (t, 1H), 7.48(d, 1H), 7.56(d, 1H), 10.90(br, 1H). |

TABLE 1-1-continued

| Compound | Structure formula | $^1$H NMR (CDCl$_3$, 300 MHz) data |
|---|---|---|
| C278-2 | | δ 0.897(d, 6H), 1.34(t, 3H), 1.98(m, 1H), 2.74(d, 2H), 4.28(d, 2H), 7.29(dd, 1H), 7.56(d, 1H), 7.85(d, 1H). |
| C305-2 | | δ 0.95m, 6H), 1.70(m, 5H), 1.96(m, 2H), 3.20 (m, 1H), 4.37(t, 2H), 7.36(d, 1H), 7.80(d, 1H), 11.10(bs, 1H). |
| C304 | | δ 1.00m, 6H), 1.40(m, 5H), 1.84(m, 2H), 3.37 (m, 1H), 4.26(t, 2H), 6.97(m, 1H), 7.24(m, 1H), 7.65(m, 1H). |
| C292 | | δ 0.90(d, 6H), 1.31(t, 3H), 2.01(m, 1H), 2.46(s, 3H), 2.78(d, 2H), 4.30(q, 2H), 6.67(d, 1H), 7.37 (d, 1H). |
| C328 | | δ 0.80(d, 6H), 1.23(t, 3H), 1.89(m, 1H), 2.66(d, 2H), 4.19(q, 2H), 7.16-7.19(2H), 7.60-7.67 (3H); |
| C279-1 | | δ 0.93(t, 3H), 1.39~1.46(m, 5H), 1.69(m, 2H), 2.99(t, 2H), 4.38(q, 2H), 7.42(d, 1H), 7.83(d, 1H). |

Example 2

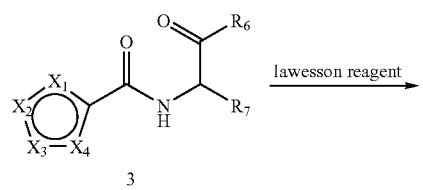

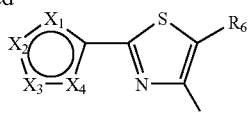

-continued

Compound 3 (0.3 mmol) was mixed with Lawesson's reagent (0.45 mmol), then THF (5 mL) was added thereto. The resulted mixture was refluxed, and the progress of reaction was tracked by TLC. Subsequently the reaction solution was cooled to room temperature, and then was concentrated to remove the solvent completely and extracted. Compound 4ii was obtained by separation through column chromatograph with petroleum ether/ethyl acetate (volume ratio 3:1) (yield 50%). The following compounds were synthesized by the same method:

TABLE 1-2

| Compound | Structure formula | $^1$H NMR (CDCl$_3$, 300 MHz) data |
|---|---|---|
| C296-1 | | δ 0.95(t, 3H), 1.35~1.48(m, 5H), 1.78(m, 2H), 3.13(t, 2H), 4.42(q, 2H), 7.45(dd, 1H), 7.80(d, 1H). |
| Wang421 | | δ 0.87(3H), 1.25-1.45(22H), 1.68-1.76(4H), 3.22(t, 2H), 4.41(q, 2H), 7.06(dd, 1H), 7.39(dd, 1H), 7.48(dd, 1H). |
| C321-2 | | δ 1.16~1.49(7H), 1.72~1.83(4H), 2.04(m, 2H), 3.74(m, 1H), 4.39(q, 2H), 7.02(dd, 1H), 7.35(d, 1H), 7.45(d, 1H). |
| C310 | | δ 0.98(d, 6H), 1.42(t, 3H), 1.98(m, 1H), 2.52(s, 1H), 3.12(d, 2H), 4.41(q, 2H), 7.50(s, 1H). |
| C324-2 | | δ 0.96(d, 6H), 1.29(t, 3H), 1.40(t, 3H), 1.97(m, 1H), 2.80(q, 2H), 3.10(d, 2H), 4.39(q, 2H), 6.98(s, 1H). |
| C328-2 | | δ 1.04(d, 6H), 1.28(t, 3H), 2.02(m, 1H), 3.16(d, 2H), 4.34(d, 2H), 6.94(s, 1H), 7.10(t, 1H), 7.21(m, 2H), 7.62(d, 1H), 10.17(br, 1H). |
| C296-3 | | δ 0.97(d, 6H), 1.41(t, 3H), 1.98(m, 1H), 3.12(d, 2H), 4.41(d, 2H), 8.12(d, 1H), 8.81(d, 1H). |
| C376 | | δ 1.02(d, 6H), 1.46(t, 3H), 2.04(m, 1H), 3.18(d, 2H), 3.91(s, 1H), 4.44(d, 2H), 7.12(d, 1H), 7.36(d, 1H), 7.95(d, 1H). |
| C352-3 | | δ 1.01(d, 6H), 1.08(d, 6H), 1.42(t, 3H), 2.03(m, 2H), 3.15(d, 2H), 3.29(d, 2H), 4.37(q, 2H), 8.61(s, 1H). |
| C223 | | δ 0.95(d, 6H), 1.86(m, 1H), 2.67(d, 2H), 7.03(t, 1H), 7.32(d, 1H), 7.39(s, 1H), 7.41(d, 1H). |

TABLE 1-2-continued
| Compound | Structure formula | $^1$H NMR (CDCl$_3$, 300 MHz) data |
|---|---|---|
| C224 | 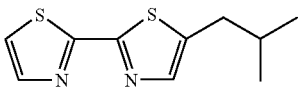 | δ 0.93(d, 6H), 1.87(m, 1H), 2.69(d, 2H), 7.34(d, 1H), 7.50(s, 1H), 7.81(d, 1H). |
| C310-2 | 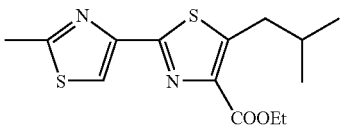 | δ 0.95(d, 6H), 1.39(t, 3H), 1.95(m, 1H), 2.77(s, 1H), 3.08(d, 2H), 4.38(d, 2H), 7.88(s, 1H). |
| C295-4 | 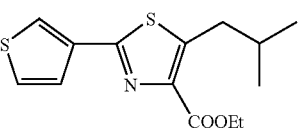 | δ 0.97(d, 6H), 1.41(t, 3H), 1.95(m, 1H), 3.09(d, 2H), 4.40(d, 2H), 7.34(m, 1H), 7.54(d, 1H), 7.83(d, 1H). |
| C310-3 | 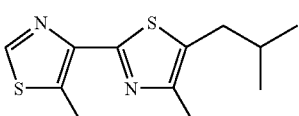 | δ 0.97(d, 6H), 1.40(t, 3H), 1.98(m, 1H), 2.92(s, 1H), 3.12(d, 2H), 4.38(d, 2H), 8.56(s, 1H). |
| C309-2 | 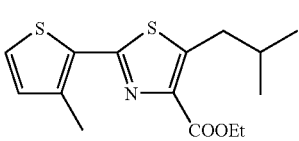 | δ 0.98(d, 6H), 1.42(t, 3H), 1.98(m, 1H), 2.49(s, 3H), 3.12(d, 2H), 4.39(d, 2H), 6.87(d, 1H), 7.25(d, 1H). |
| C396 | 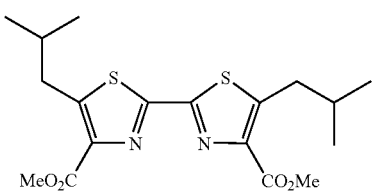 | δ 0.99(d, 12H), 2.00(m, 2H), 3.17(d, 4H), 3.95(s, 6H). |
| C337 | 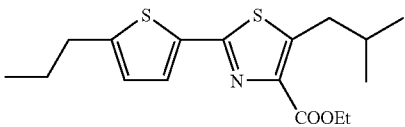 | δ 0.97(d, 9H), 1.40(t, 5H), 1.73(m, 2H), 1.95(m, 1H), 2.77(t, 2H), 3.08(d, 2H), 4.39(q, 2H), 6.71(d, 1H), 7.28(d, 1H). |
| C243 | 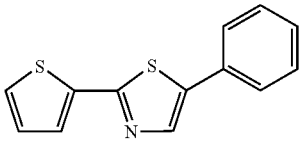 | δ 7.09(m, 1H), 7.36(m, 1H), 7.43(m, 3H), 7.52(d, 1H), 7.57(m, 2H), 7.92(s, 1H). |
| C322 | 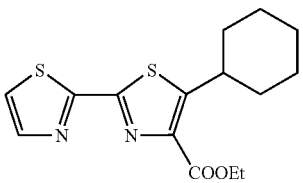 | δ 1.39m, 6H), 1.42(m, 5H), 1.80(m, 2H), 3.75(m, 1H), 4.41(t, 2H), 7.43(d, 1H), 7.84(d, 1H) |
| C295-1 | 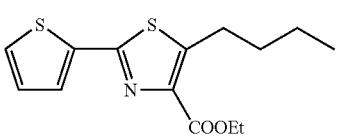 | δ 0.94t, 3H), 1.41(t, 3H), 1.42(m, 2H), 1.68(m, 2H), 3.21(t, 2H), 4.40(q, 2H), 7.04(dd, 1H), 7.38(dd, 1H), 7.46(dd, 1H) |

TABLE 1-2-continued

| Compound | Structure formula | $^1$H NMR (CDCl$_3$, 300 MHz) data |
|---|---|---|
| C296-2 | | δ 0.91(t, 3H), 1.39(t, 3H), 1.44(m, 2H), 1.68(m, 2H), 3.22(t, 2H), 4.39(q, 2H), 7.43(d, 1H), 7.82(d, 1H) |
| C352-2 | | δ 0.90(d, 6H), 0.96(d, 6H), 1.33(t, 3H), 2.25(m, 2H), 2.62(d, 2H), 3.10(d, 2H), 4.38(d, 2H), 6.96(s, 1H). |
| C309 | | δ 0.95(d, 6H), 1.38(t, 3H), 1.92(m, 1H), 2.46(s, 3H), 3.05(d, 2H), 4.36(q, 2H), 6.67(d, 1H), 7.24(d, 1H). |
| C345 | | δ 1.00(d, 6H), 1.44(t, 3H), 1.99(dq, 1H), 3.13(d, 2H), 4.43(q, 2H), 7.34-7.39, (m, 2H), 7.40(s, 1H), 7.76-7.79 (m, 1H), 7.81-7.84(m, 1H). |

Example 3

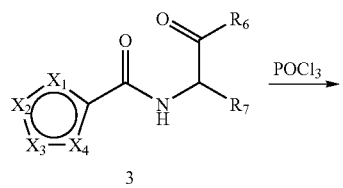

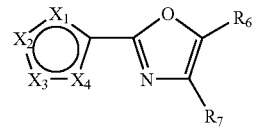

Compound 3 (0.3 mmol) was mixed with POCl$_3$ (3 mL), and heated to 80° C. The progress of reaction was tracked by TLC. Subsequently the reaction solution was poured into sodium bicarbonate (NaHCO$_3$) solution of 0° C., and POCl$_3$ was removed. Then the reactant was extracted with ethyl acetate, and the solvent was removed completely by concentration. Compound 4iii was obtained by separation through column chromatograph with petroleum ether/ethyl acetate (volume ratio 4:1) (yield 80%). The following compounds were synthesized by the same method:

TABLE 1-3

| Compound | Structural formula | $^1$H NMR (CDCl$_3$, 300 MHz) data |
|---|---|---|
| C280-1 | | δ 0.94(t, 3H), 1.35~1.48(m, 5H), 1.76(m, 2H), 3.13(t, 2H), 4.42(q, 2H), 7.52(d, 1H), 7.96(d, 1H). |
| C279-3 | | δ 0.94(t, 3H), 1.33~1.44(bm, 5H), 1.73(m, 2H), 3.07(t, 2H), 4.40(q, 2H), 7.10(dd, 1H), 7.43(d, 1H), 7.72(d, 1H). |

TABLE 1-3-continued

| Compound | Structural formula | $^1$H NMR (CDCl$_3$, 300 MHz) data |
|---|---|---|
| C263-2 | | δ 1.42(t, 3H), 2.00(d, 3H), 4.42(q, 2H), 6.64(m, 1H), 6.96(d, 1H), 7.11(dd, 1H), 7.45(d, 1H), 7.76(d, 1H). |
| C325 | | δ 1.47(t, 3H), 4.47(q, 2H), 7.15(dd, 1H), 7.34~7.43(m, 3H), 7.50(d, 1H), 7.58~7.67(m, 2H), 7.85(d, 1H). |
| C305-1 | | δ 1.22~1.45(m, 7H), 1.54~1.75(m, 2H), 1.82~1.93 (m, 4H), 3.47(m, 1H), 4.38(q, 2H), 7.08(dd, 1H), 7.41(d, 1H), 7.69(d, 1H). |
| C321-1 | | δ 0.91~1.00(m, 6H), 1.37~1.45(m, 5H), 1.65~1.76(m, 4H), 2.78(t, 2H), 3.05(t, 2H), 4.40 (q, 2H), 6.77(d, 1H), 7.53(d, 1H). |
| C321-3 | | δ 0.95(d, 9H), 1.37(t, 5H), 1.70(m, 2H), 2.07(m, 1H), 2.77(t, 2H), 2.90(d, 2H), 4.36(q, 2H), 6.74(d, 1H), 7.50(d, 1H). |
| C208 | | δ 0.97(d, 6H), 2.06(m, 1H), 2.61(d, 2H), 6.91(s, 1H), 7.43(d, 2H), 7.92(d, 1H). |
| C294 | | δ 0.92(d, 6H), 1.40(t, 3H), 2.10(m, 1H), 2.19(s, 3H), 2.97(d, 2H), 4.36(d, 2H), 8.64(s, 1H). |
| C293-2 | | δ 0.98(d, 6H), 1.40(t, 3H), 2.09(m, 1H), 2.57(s, 3H), 2.95(d, 2H), 4.37(d, 2H), 6.88(d, 1H), 7.28(d, 1H). |
| C279-4 | | δ 0.99(d, 6H), 1.40(t, 3H), 2.12(m, 1H), 2.96(d, 2H), 4.40(d, 2H), 7.37(m, 1H), 7.65(d, 1H), 7.98(d, 1H). |
| C227 | | δ 7.14(q, 1H), 7.35(m, 1H), 7.40(s, 1H), 7.50(m, 3H), 7.70(m, 2H), 7.74(d, 1H). |

TABLE 1-3-continued

| Compound | Structural formula | $^1$H NMR (CDCl$_3$, 300 MHz) data |
| --- | --- | --- |
| C307 | | δ 0.92(d, 6H), 1.30(m, 6H), 2.06(m, 1H), 2.83(m, 2H), 2.91(d, 2H), 4.36(t, 2H), 7.65(d, 1H), 7.51(d, 1H). |
| C306 | | δ 1.22m, 6H), 1.50(m, 5H), 1.82(m, 2H), 3.48(m, 1H), 4.39(t, 2H), 7.50(d, 1H), 7.94(d, 1H); |
| C280-2 | | δ 0.94(t, 3H), 1.35~1.48(m, 5H), 1.76(m, 2H), 3.13(t, 2H), 4.42(q, 2H), 7.52(d, 1H), 7.96(d, 1H) |
| C279-2 | | δ 0.95(t, 3H), 1.40(t, 3H), 1.40(m, 2H), 1.71(m, 2H), 3.07(t, 2H), 4.40(q, 2H), 7.10(dd, 1H), 7.43(dd, 1H), 7.72(dd, 1H) |
| C293 | | δ 0.95(d, 6H), 1.38(t, 3H), 1.92(m, 1H), 2.46(s, 3H), 3.05(d, 2H), 4.36(q, 2H), 6.67(d, 1H), 7.24(d, 1H). |
| C329 | | δ 1.00(d, 6H), 1.40(t, 3H), 2.13(dq, 6.9 Hz, 1H), 2.97(d, 2H), 4.40(q, 3H), 7.33-7.39(m, 2H), 7.79-7.84(m, 2H), 7.93(s, 1H). |

Example 4

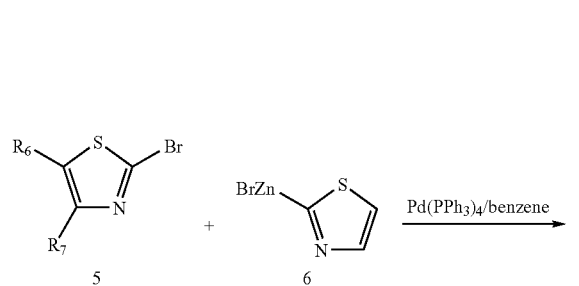

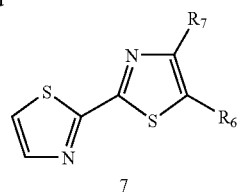

Compound 5 (1.6 mmol) was dissolved in benzene (10 mL), then solution of compound 6 (3.2 mmol) in THF (4 mL) and tetrakis(triphenylphosphine)palladium (Pd(PPh$_3$)$_4$) (10 mg) were added thereto in turn, and heated to 100° C. The reaction was tracked by TLC. The reaction solution was concentrated, and compound 7 (Wang282-1) was obtained by separation through column chromatograph with petroleum ether/ethyl acetate (volume ratio 3:1) (yield 25). The following compounds were synthesized by the same method:

TABLE 1-4

| Compound | Structure formula | $^1$H NMR (CDCl$_3$, 300 MHz) data |
| --- | --- | --- |
| Wang282-1 | | δ 0.99 (d, 6H), 1.99 (m, 1H), 3.15 (d, 2H), 3.96 (s, 3H), 7.46 (d, 1H), 7.86 (d, 1H). |
| Wang368 | | δ 4.00 (s, 3H), 4.70 (s, 2H), 6.96 (dd, 1H), 7.65 (d, 1H), 7.33 (dd, 1H), 7.46 (d, 1H), 7.83 (d, 1H). |
| Wang354 | | δ 3.83 (s, 3H), 7.09 (dd, 1H), 7.29 (d, 1H), 7.41 (dd, 1H), 7.54 (d, 1H), 7.92 (d, 1H). |
| Wang240 | | δ 1.38 (t, 3H), 4.40 (q, 2H), 7.48 (d, 1H), 7.86 (d, 1H), 8.20 (s, 1H). |
| Wang222 | | δ 1.89 (t, 4H), 2.83 (m, 4H), 7.37 (d, 1H), 7.83 (d, 1H). |
| Wang284 | | δ 3.41 (s, 3H), 3.55 (t, 2H), 3.68 (t, 2H), 3.96 (s, 3H), 7.46 (d, 1H), 7.88 (d, 1H). |
| Wang316 | | δ 3.98 (s, 3H), 4.60 (s, 2H), 7.30 (5H), 7.43 (d, 1H), 7.82 (d, 1H). |
| Wang352 | | δ 4.00 (s, 3H), 4.72 (s, 2H), 6.97 (ddd, 1H), 7.17 (dd, 1H), 7.25 (s, 1H), 7.34 (dd, 1H), 7.77 (s, 1H) |
| Wang338 | | δ 3.84 (s, 3H), 7.09 (ddd, 1H), 7.28 (dd, 1H), 7.33 (d, J = 0.6 Hz, 1H), 7.4 (dd, 1H), 7.84 (d, 1H). |

TABLE 1-4-continued

| Compound | Structure formula | $^1$H NMR (CDCl$_3$, 300 MHz) data |
|---|---|---|
| Wang354 | (structure: thiazole-thiazole-COOMe with 2-Cl-4-F-phenyl) | δ 3.83 (s, 3H), 7.10 (ddd, 1H), 7.28 (dd, 1H), 7.41 (dd, 1H), 7.54 (d, 1H), 7.93 (d, 1H). |
| Wang282 | (structure: thiazole-thiazole-COOMe with butyl) | δ 0.92 (t, 3H), 1.45 (tq, 2H), 1.70 (tt, 2H), 3.25 (t, 2H), 3.92 (s, 3H), 7.43 (dd, 1H), 7.84 (d, 1H). |

Example 5

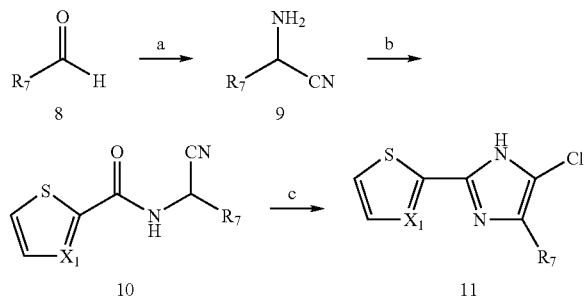

a 25% NH$_4$OH, KCN, NH$_4$Cl;
b EDC, DMAP, DMF, Thiazole-2-carboxylic acid or Thiophene-2-carboxylic acid
c PPh$_3$, CCl$_4$, CH$_3$CN Benzoic aldehyde (25 mmol) was added to the 25% ammonia water solution (20 mL) containing potassium cyanide (KCN) (30 mmol) and ammonium chloride (37.5 mmol). The resulted mixture was stirred for 56 hours, and the reaction was tracked by TLC. The reactant was extracted with dichloromethane. Then the extract was dried over magnesium sulphate (MgSO$_4$), and the solvent was concentrated to obtain compound 9 (2.9 g, yield 90%). Compound 9 (6 mmol) was mixed with EDC (7.8 mmol), DMAP (0.6 mmol) and thiazole-2-formic acid (6 mmol). The resulted mixture was cooled under ice bath (0° C.), subsequently DMF was added thereto (15 mL). The progress of reaction was tracked by TLC. After the reaction was completed, the reactant was diluted with water, and extracted with ethyl acetate. The solvent was removed completely by concentration, and compound 10 was obtained by separation through column chromatograph (0.76 g, yield 50). Compound 10 (3.1 mmol) was mixed with triphenylphosphine (Ph$_3$P) (7.75 mmol) and carbon tetrachloride (CCl$_4$) (7.75 mmol), and the resulted mixture was dissolved in acetonitrile (20 mL). The reaction was conducted at 45° C. and tracked by TLC. After the reaction was completed, the solvent was removed by concentration, and compound 11 (Wang261) (yield 60%) was obtained by separation through column chromatograph with petroleum ether/ethyl acetate (volume ratio 5:1). The following compounds were synthesized by the same method:

TABLE 1-5

| Compound | Structure Formula | $^1$H NMR (CDCl$_3$, 300 MHz) data |
|---|---|---|
| Wang261 | (structure: thiazole-imidazole with Cl and Ph) | δ 7.34 (d, 1H), 7.40 (m, 3H), 7.63 (d, 1H), 7.69 (d, 2H). |
| Wang260 | (structure: thiophene-imidazole with Cl and Ph) | δ 7.00 (dd, 1H), 7.35 (m, 4H), 7.59 (dd, 1H), 7.72 (dd, 2H). |

TABLE 1-5-continued

| Compound | Structure Formula | $^1$H NMR (CDCl$_3$, 300 MHz) data |
|---|---|---|
| Wang241 | | δ 0.77 (t, 3H), 1.16 (m, 2H), 1.23 (m, 3H), 2.48 (t, 2H), 7.36 (d, 1H), 7.44 (d, 1H), 12.27 (bs, 1H). |

Example 6

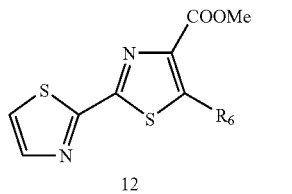

12

LiOH, MeOH, H$_2$O →

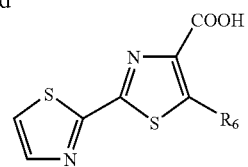

13

Compound 12 (1 mmol) was mixed with lithium hydroxide (LiOH) (4 mmol), and the mixed solvent of MeOH and water was added thereto. The reaction was conducted at room temperature and tracked by TLC. After the reaction was completed, the solvent was concentrated, acidified with 1 mol/L hydrochloric acid, and extracted with ethyl acetate. The solvent was removed completely by concentration, and compound 13 (Wang268) was obtained (yield 98%). The following compounds were synthesized by the same method:

TABLE 1-6

| Compound | Structure formula | $^1$H NMR (CDCl$_3$, 300 MHz) data |
|---|---|---|
| Wang268 | | δ 0.76 (t, 3H), 1.13 (m, 2H), 1.38 (m, 2H), 2.47 (t, 2H), 7.36 (d, 1H), 7.74 (d, 1H). |
| Wang302 | | δ 4.89 (s, 2H), 7.27 (5H), 7.38 (d, 1H), 7.80 (d, 1H). |
| Wang268-1 | | δ 0.11 (d, 6H), 2.03 (m, 1H), 3.33 (d, 2H), 7.40 (d, 1H), 7.80 (d, 1H). |

Example 7

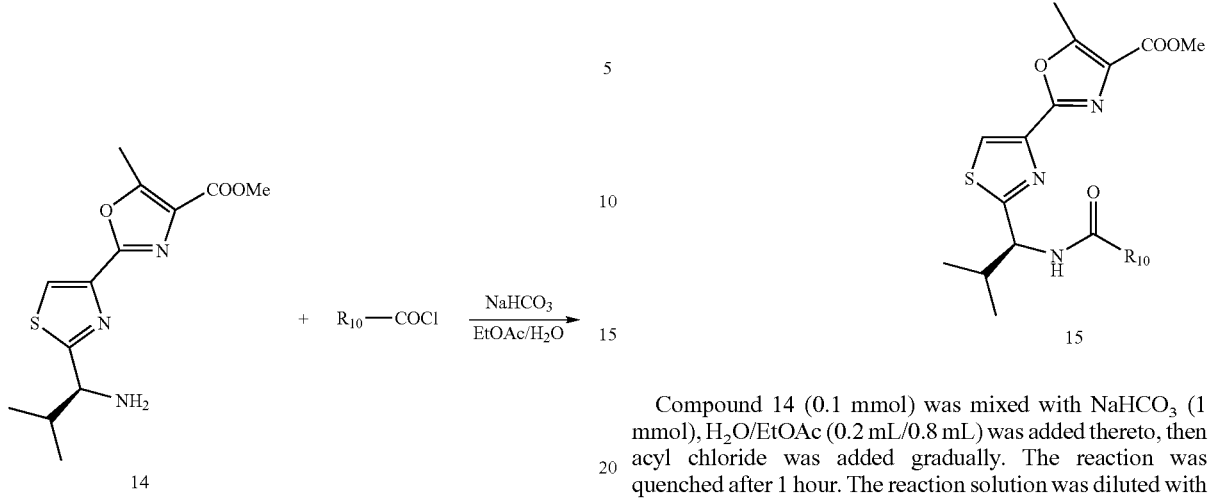

Compound 14 (0.1 mmol) was mixed with NaHCO$_3$ (1 mmol), H$_2$O/EtOAc (0.2 mL/0.8 mL) was added thereto, then acyl chloride was added gradually. The reaction was quenched after 1 hour. The reaction solution was diluted with EtOAc, and the aqueous phase was extracted EtOAc. The organic phases were combined, washed with saturated NaCl solution 3 times, dried over MgSO$_4$, and concentrated to remove the solvent completely. The mixture was purified through column chromatography to obtain the product 15 (Wang363.43-1). The yield was 83%. The following compounds were synthesized by the same method:

TABLE 1-7

| Compound | Structure formula | $^1$H NMR (CDCl$_3$, 300 MHz) data |
|---|---|---|
| Wang363.43-1 | | δ 0.68-0.79 (4H), 0.92 (3H), 0.95 (d, 3H), 1.44-1.49 (1H), 2.35-2.42 (1H), 2.70 (3H), 3.91 (3H), 5.23 (1H), 6.58 (1H), 7.95 (s, 1H). |
| Yao393.50 | | δ 0.82 (3H), 0.89 (d, 3H), 0.90 (d, 3H), 1.26 (m, 4H), 1.59 (m, 2H), 2.22 (t, 2H), 2.36 (m, 1H), 2.67 (s, 3H), 3.89 (s, 3H), 5.20 (dd, 1H), 6.40 (d, 1H), 7.93 (s, 1H) |

TABLE 1-7-continued
| Compound | Structure formula | ¹H NMR (CDCl₃, 300 MHz) data |
| --- | --- | --- |
| Wang391.49-1 | 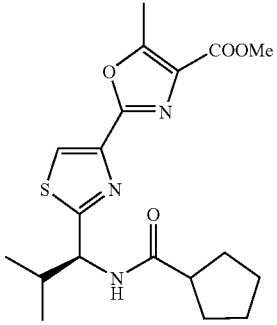 | δ 0.92 (d, 6H), 1.56 (m, 2H), 1.69-1.87 (6H), 2.40 (m, 1H), 2.61 (m, 1H), 2.69 (s, 3H), 3.90 (s, 3H), 5.22 (dd, 1H), 6.29 (d, 1H), 7.95 (s, 1H) |
| Wang377.46-1 | 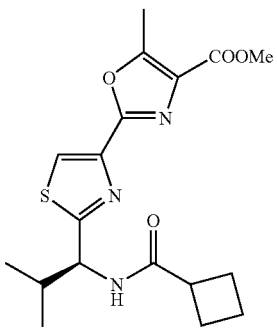 | δ 0.92 (d, 3H), 0.93 (d, 3H), 2.01 (m, 2H), 2.18 (m, 2H), 2.26 (m, 2H), 2.40 (m, 1H), 2.71 (s, 3H), 3.08 (m, 1H), 3.92 (s, 3H), 5.22 (dd, 1H), 6.15 (d, 1H), 7.96 (s, 1H) |
| Wang405.51-1 | 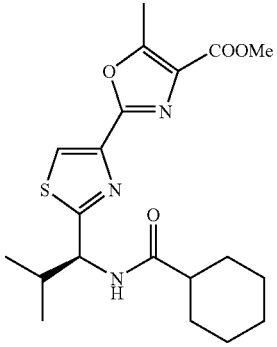 | δ 0.91 (d, 6H), 1.19-1.28 (m, 2H), 1.43 (m, 2H), 1.65-1.84 (m, 6H), 2.17 (m, 1H), 2.40 (m, 1H), 2.69 (s, 3H), 3.90 (s, 3H), 5.22 (dd, 1H), 6.32 (d, 1H), 7.95 (s, 1H); |
| Wang417.46-J | 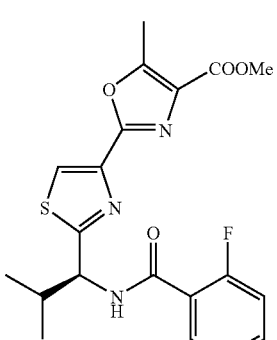 | δ 1.01 (d, 3H), 1.06 (d, 3H), 2.52 (m, 1H), 2.73 (s, 3H), 3.94 (s, 3H), 5.42 (dd, 1H), 7.10 (d, 1H), 7.16 (ddd, 1H), 7.40 (ddd, 1H), 7.55 (ddd, 1H), 7.58 (d, 1H), 7.99 (s, 1H). |

TABLE 1-7-continued

| Compound | Structure formula | ¹H NMR (CDCl₃, 300 MHz) data |
| --- | --- | --- |
| Wang417.46-p | | δ 1.01 (d, 3H), 1.06 (d, 3H), 2.52 (m, 1H), 2.73 (s, 3H), 3.94 (s, 3H), 5.42 (dd, 1H), 7.10 (d, 1H), 7.16 (ddd, 1H), 7.40 (ddd, 1H), 7.55 (ddd, 1H), 7.58 (d, 1H), 7.99 (s, 1H). |
| Wang443.52 | | δ 0.94 (d, 3H), 0.95 (d, 3H), 2.50 (m, 1H), 2.68 (s, 3H), 3.92 (s, 3H), 3.99, 4.07 (dd, 2H), 4.59, 4.64 (dd, 2H), 5.24 (dd, 1H), 7.29-7.34 (5H), 8.00 (s, 1H) |
| Yao351.42 | | δ 0.88 (d, 3H), 0.90 (d, 3H), 1.24 (t, 3H), 2.26 (q, 3H), 2.38 (m, 1H), 2.66 (s, 3H), 3.88 (s, 3H), 5.19 (dd, 1H), 6.44 (d, 1H), 7.92 (s, 1H) |
| Wang413.49 | | δ 0.75 (d, 3H), 0.86 (d, 3H), 2.38 (m, 1H), 2.70 (s, 3H), 3.64 (s, 2H), 3.91 (s, 3H), 5.19 (dd, 1H), 6.24 (d, 1H), 7.27-7.38 (5H), 7.95 (s, 1H) |

TABLE 1-7-continued
| Compound | Structure formula | $^1$H NMR (CDCl$_3$, 300 MHz) data |
|---|---|---|
| Yao379.47 | | δ 0.88 (d, 3H), 0.94 (d, 3H), 1.94 (s, 9H), 2.47 (m, 1H), 2.66 (s, 3H), 3.88 (s, 3H), 5.18 (m, 1H), 6.32 (d, 1H), 7.94 (s, 1H) |
| Yao337.40 | | δ 0.88 (d, 3H), 0.91 (d, 3H), 2.03 (s, 3H), 2.33 (m, 1H), 2.67 (s, 3H), 3.88 (s, 3H), 5.18 (dd, 1H), 6.60 (d, 1H), 7.92 (s, 1H) |
| Wang399.46 | | δ 1.02 (d, 3H), 1.06 (d, 3H), 2.55 (m, 1H), 2.73 (s, 3H), 3.94 (s, 3H), 5.46 (dd, 1H), 6.95 (d, 1H), 7.44-7.54 (m, 3H), 7.84 (d, 2H), 8.01 (s, 1H) |
Example 8
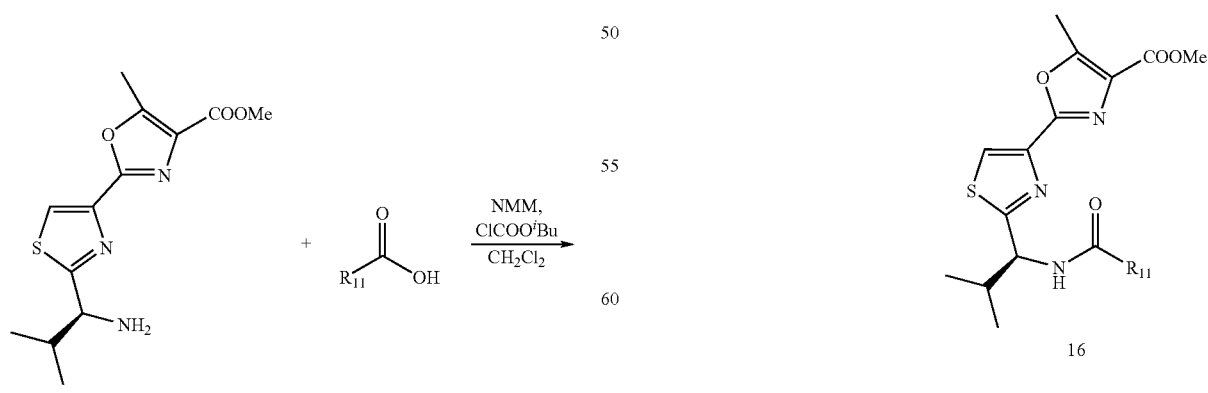
Acid (0.12 mmol) was dissolved in CH$_2$Cl$_2$ (2 mL), and cooled in ice salt bath (0° C.). After 10 minutes, N-methylmorpholine (NMM) (0.15 mmol) and isobutyl chloroformate (ClCOO^iBu) (0.13 mmol) were added thereto in turn. Then stir was continued for half an hour, compound 14 (0.1 mmol) was added thereto. Stir was continued, and the system was heated to room temperature gradually. The reaction was tracked by TLC. The reaction was quenched with water after the reaction was completed. The reactant was extracted with EtOAc. The EtOAc phase was washed 3 times with saturated salt solution, dried over $MgSO_4$, and the solvent was concentrated. The mixture was purified through column chromatography (petroleum ether/ethyl acetate (volume ratio 2:1)) to obtain product 16 (Wang363.43-2). The yield was 55%. The following compounds were synthesized by the same method:

TABLE 1-8

| Compound | Structure formula | $^1$H NMR (CDCl$_3$, 300 MHz) data |
| --- | --- | --- |
| Wang363.43-2 | | δ 0.90 (d, 3H), 0.91 (d, 3H), 2.45 (m, 1H), 2.69 (s, 3H), 3.05-3.08 (m, 2H), 3.90 (s, 3H), 5.16-5.26 (m, 3H), 5.87-6.00 (m, 1H), 6.47 (d, 1H), 7.96 (s, 1H). |
| Wang403.50 | | δ 0.89 (d, 3H), 0.92 (d, 3H), 1.89 (m, 2H), 2.27-2.37 (m, 4H), 2.44 (m, 1H), 2.69 (s, 3H), 3.10 (s, 2H), 3.91 (s, 3H), 5.20 (dd, 6.3 Hz, 1H), 5.63 (m, 1H), 6.51 (d, 1H), 7.91 (s, 1H) |
| Wang417.52 | | δ 0.89 (d, 3H), 0.93 (d, 3H), 1.55-1.64 (m, 4H), 1.97 (m, 2H), 2.07 (m, 2H), 2.46 (m, 1H), 2.70 (s, 3H), 2.94 (s, 2H), 3.92 (s, 3H), 5.21 (dd, 6.0 Hz, 1H), 5.69 (brs, 1H), 6.59 (d, 1H), 7.99 (s, 1H) |
| Wang377.46-2 | | δ 0.88 (d, 3H), 0.89 (d, 3H), 2.30-2.35 (5H), 2.67 (s, 3H), 3.88 (s, 3H), 4.94 (dd, 1H), 5.01 (dd, 1H), 5.19 (dd, 1H), 5.76 (m, 1H), 6.50 (d, 1H), 7.92 (s, 1H) |

TABLE 1-8-continued

| Compound | Structure formula | ¹H NMR (CDCl₃, 300 MHz) data |
|---|---|---|
| Wang391.49-2 | 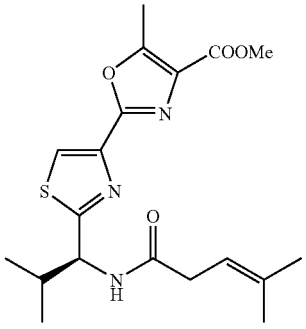 | δ 0.87 (d, 3H), 0.92 (d, 3H), 1.66 (s, 3H), 1.79 (s, 3H), 2.44 (m, 1H), 2.69 (s, 3H), 3.01 (d, 2H), 3.91 (s, 3H), 5.19 (dd, 1H), 5.33 (t, 1H), 6.51 (d, 1H), 7.97 (s, 1H) |
| Yao405.51 | 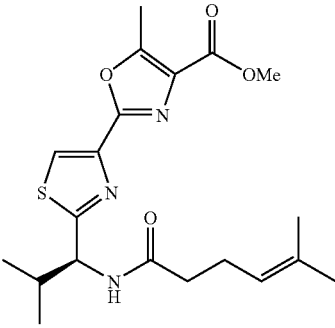 | δ 0.89 (d, 3H), 0.90 (d, 3H), 1.56 (s, 3H), 1.61 (s, 3H), 2.23-2.67 (m, 5H), 2.74 (s, 3H), 3.89 (s, 3H), 5.05 (m, 1H), 5.20 (dd, 1H), 6.45 (d, 1H), 7.94 (s, 1H) |

Exampl 9

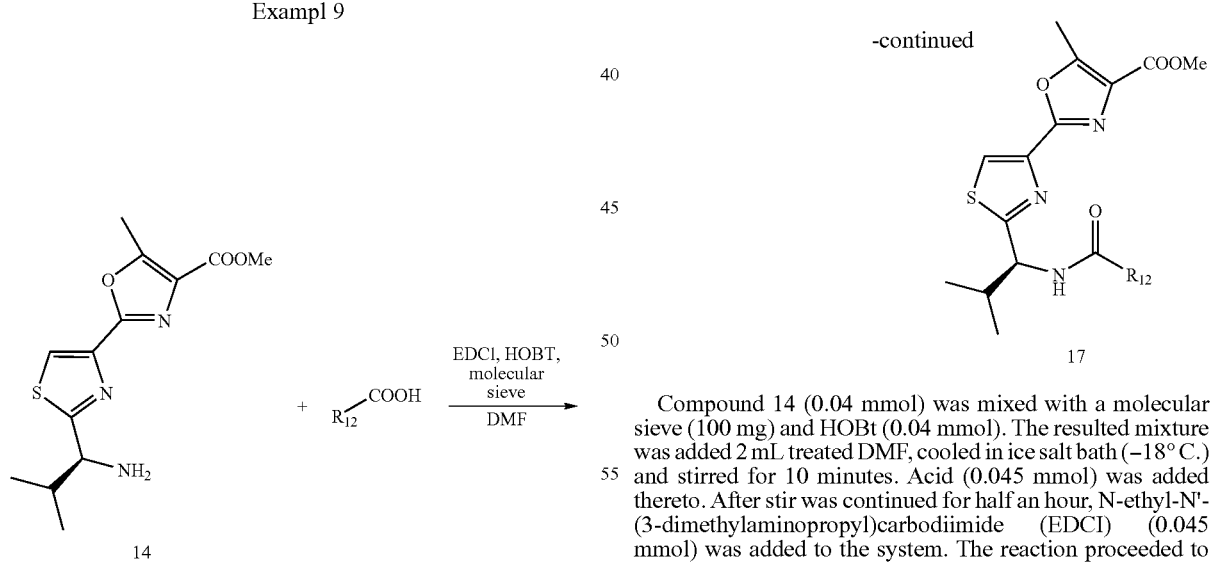

Compound 14 (0.04 mmol) was mixed with a molecular sieve (100 mg) and HOBt (0.04 mmol). The resulted mixture was added 2 mL treated DMF, cooled in ice salt bath (−18° C.) and stirred for 10 minutes. Acid (0.045 mmol) was added thereto. After stir was continued for half an hour, N-ethyl-N'-(3-dimethylaminopropyl)carbodiimide (EDCI) (0.045 mmol) was added to the system. The reaction proceeded to react for half an our in ice salt bath, and the system was heated to room temperature. The reaction was tracked by TLC. After the reaction was completed, the system was diluted with 50 mL EtOAc. The EtOAc phase was washed with 100 mL water and saturated NaCl solution 3 times respectively, dried over MgSO₄, and the solvent was concentrated. The mixture was purified through column chromatography (petroleum ether/ethyl acetate=2:1 (volume ratio)) to obtain the product 17 (Wang405.49). The yield was 96%. The following compounds were synthesized by the same method:

TABLE 1-9
| Compound | Structure formula | ¹H NMR (CDCl₃, 300 MHz) data |
|---|---|---|
| Wang405.49 | 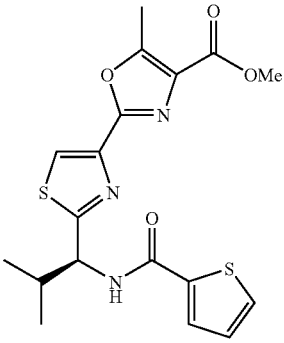 | δ 0.97 (d, 3H), 1.03 (d, 3H), 2.51 (m, 1H), 2.71 (s, 3H), 3.92 (s, 3H), 5.35 (dd, 1H), 6.87 (d, 1H), 7.07 (dd, 1H), 7.49 (d, 1H), 7.60 (d, 1H), 7.98 (s, 1H). |
| Wang515.18 | 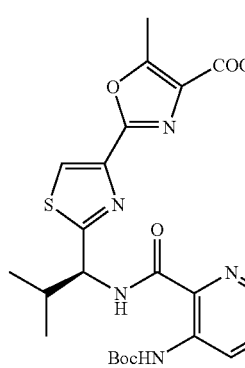 | δ 1.01 (d, 6H), 1.46 (s, 9H), 2.67 (m, 1H), 2.69 (s, 3H), 3.90 (s, 3H), 5.33 (dd, 6 Hz, 1H), 7.38 (dd, 1H), 8.15 (dd, 1H), 8.82 (dd, 1H), 9.05 (d, 1H), 11.01 (s, 1H) |
| Wang429.49 | 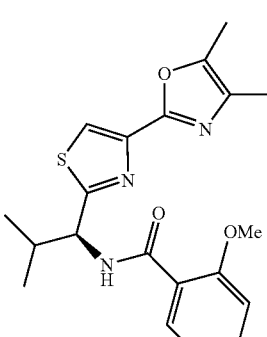 | δ 0.97 (d, 3H), 1.02 (d, 3H), 2.62 (m, 1H), 2.69 (s, 3H), 3.89 (s, 3H), 4.03 (s, 3H), 5.49 (dd, 1H), 6.99 (d, 1H), 7.05 (t, 1H), 7.44 (dd, 1H), 7.96 (s, 1H), 8.16 (d, 1H), 8.70 (d, 1H) |

TABLE 1-9-continued

| Compound | Structure formula | $^1$H NMR (CDCl$_3$, 300 MHz) data |
|---|---|---|
| Yao415 | 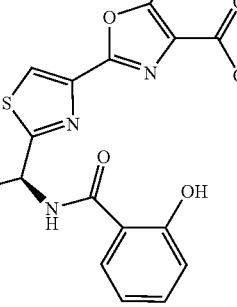 | δ 1.00 (d, 3H), 1.07 (d, 3H), 2.52 (m, 1H), 2.73 (s, 3H), 3.94 (s, 3H), 5.40 (dd, 1H), 6.90 (t, 1H), 6.99 (d, 1H), 7.22 (d, 1H), 7.42 (t, 1H), 7.53 (d, 1H), 8.02 (s, 1H). |
| Wang577.72 | 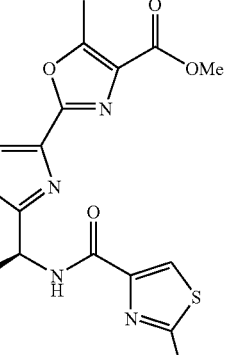 | δ 0.94 (d, 3H), 1.01~1.06 (9H), 1.45 (s, 9H), 2.39 (m, 1H), 2.66 (m, 1H), 2.73 (s, 3H), 3.94 (s, 3H), 4.90 (m, 1H), 5.15 (m, 1H), 5.36 (dd, 1H), 7.93 (d, 1H), 8.01 (s, 1H), 8.04 (s, 1H). |

Example 10

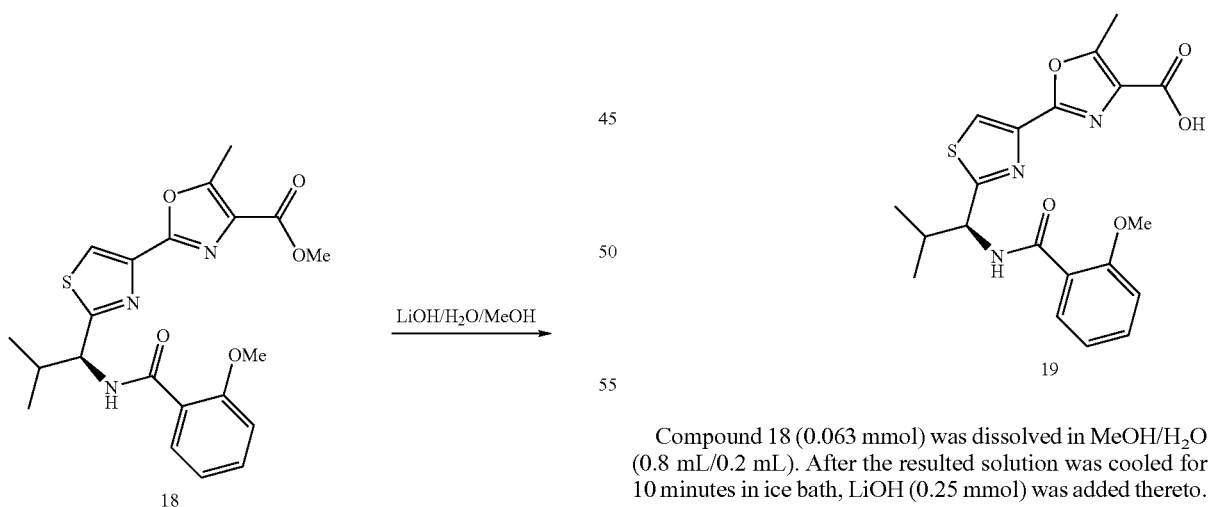

Compound 18 (0.063 mmol) was dissolved in MeOH/H$_2$O (0.8 mL/0.2 mL). After the resulted solution was cooled for 10 minutes in ice bath, LiOH (0.25 mmol) was added thereto. The system was heated to room temperature gradually, and the reaction was tracked by TLC. After the methyl ester reaction was completed, the reaction solution was concentrated, then water was added to dilute, acidified to acidity with HCl, extracted with EtOAc. The organic phase was washed 3 times with saturated NaCl, dried over MgSO$_4$, and the solvent was concentrated to obtain product 19 (Wang415.46). The following compounds were synthesized by the same method.

TABLE 1-10

| Compound | Structure formula | $^1$H NMR (CDCl$_3$, 300 MHz) data |
|---|---|---|
| Wang415.46 | | δ 1.02 (d, 3H), 1.07 (d, 3H), 2.67 (m, 1H), 2.75 (s, 3H), 4.07 (s, 3H), 5.54 (dd, 1H), 7.04 (d, 1H), 7.11 (dt, 1H), 7.48 (td, 1H), 7.99 (s, 1H), 8.22 (dd, 1H), 8.75 (d, 1H). |
| Wang377.46-OH | | δ 0.97 (d, 6H), 1.60-1.89 (8H), 2.44 (m, 1H), 2.62 (m, 1H), 2.75 (s, 3H), 5.26 (dd, 1H), 6.26 (d, 1H), 7.97 (s, 1H). |
| Wang389.47 | | δ 0.94 (d, 3H), 0.97 (d, 3H), 1.88-1.99 (m, 2H), 2.31-2.33 (m, 2H), 2.37-2.44 (m, 2H), 2.46-2.53 (m, 1H), 2.75 (s, 3H), 3.14 (s, 2H), 5.24 (dd, 1H), 5.67 (m, 1H), 7.98 (s, 1H). |

Example 11

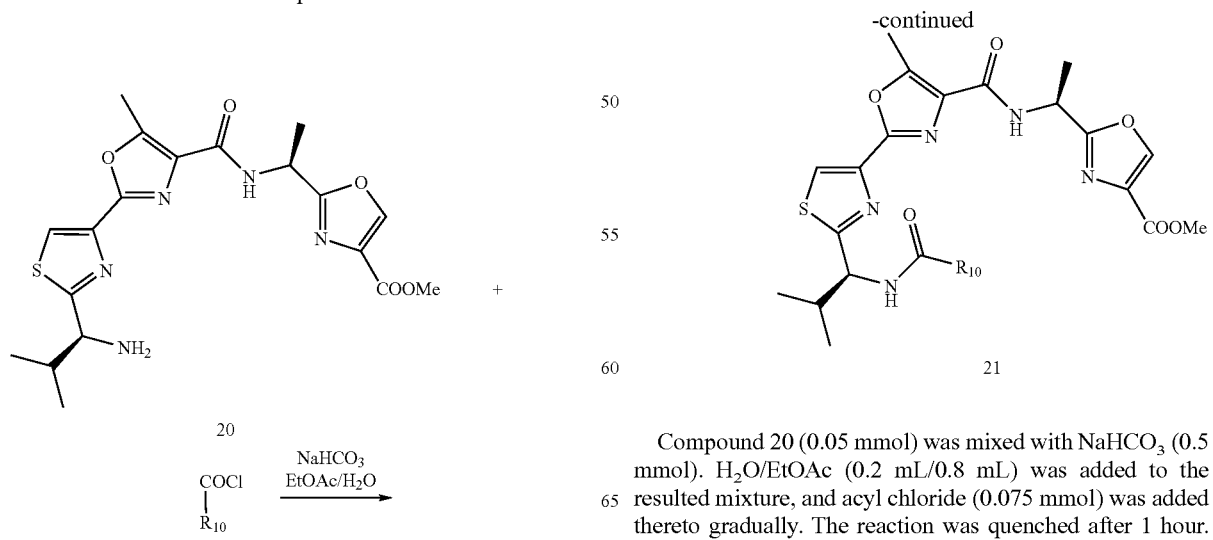

Compound 20 (0.05 mmol) was mixed with NaHCO$_3$ (0.5 mmol). H$_2$O/EtOAc (0.2 mL/0.8 mL) was added to the resulted mixture, and acyl chloride (0.075 mmol) was added thereto gradually. The reaction was quenched after 1 hour. The reaction solution was diluted with EtOAc, and the aqueous phase was extracted 2 times with EtOAc. EtOAc phases were combined, washed 3 times with saturated NaCl solution, dried over MgSO$_4$, and the solvent was concentrated. The mixture was purified through column chromatography (petroleum ether/ethyl acetate (volume ratio 1:1)) to obtain product 21 (Wang537.59). The yield was 75%. The following compounds were synthesized by the same method:

TABLE 1-11

| Compound | Structure formula | $^1$H NMR (CDCl$_3$, 300 MHz) data |
| --- | --- | --- |
| Wang537.59 | | δ 1.01 (d, 3H), 1.05 (d, 3H), 1.68 (d, 3H), 2.59 (m, 1H), 2.7 (s, 3H), 3.88 (s, 3H), 5.46 (m, 1H), 5.49 (m, 1H), 6.97 (d, 1H), 7.41-7.54 (m, 4H), 7.81-7.83 (m, 1H), 7.82 (d, 1H), 7.87 (s, 1H), 8.17 (s, 1H). |
| Wang531.63 | | δ 0.86 (m, 3H), 0.96 (d, 6H), 1.31 (m, 4H), 1.63 (m, 2H), 1.67 (d, 3H), 2.26 (t, 2H), 2.46 (m, 1H), 2.71 (s, 3H), 3.90 (s, 3H), 5.25 (dd, 1H), 5.50 (m, 1H), 6.26 (d, 1H), 7.52 (d, 1H), 7.86 (s, 1H), 8.18 (s, 1H) |
| Wang517.60 | | δ 0.94 (d, 3H), 0.97 (d, 3H) 1.25 (s, 9H), 1.69 (d, 3H), 2.56 (m, 1H), 2.71 (s, 3H), 3.89 (s, 3H), 5.24 (dd, 6.0 Hz, 1H), 5.49 (m, 1H), 6.30 (d, 1H), 7.52 (d, 1H), 7.85 (s, 1H), 8.17 (s, 1H) |
| Wang475.52 | | δ 0.95 (d, 3H), 0.97 (d, 3H) 1.69 (d, 3H), 2.08 (s, 3H), 2.42 (m, 1H), 2.71 (s, 3H), 3.90 (s, 3H), 5.23 (dd, 1H), 5.50 (m, 1H), 6.39 (d, 1H), 7.54 (d, 1H), 7.86 (s, 1H), 8.18 (s, 1H) |

TABLE 1-11-continued

| Compound | Structure formula | ¹H NMR (CDCl₃, 300 MHz) data |
|---|---|---|
| Wang489.55 | | δ 0.94 (d, 3H), 0.95 (d, 3H), 1.70 (t, 3H), 2.30 (q, 2H), 2.43 (m, 1H), 2.70 (s, 3H), 3.89 (s, 3H), 5.24 (dd, 1H), 5.49 (m, 1H), 6.32 (d, 1H), 7.53 (d, 1H), 7.85 (s, 1H), 8.17 (s, 1H) |
| Wang515.58-3 | | δ 0.95 (d, 3H), 0.96 (d, 3H) 1.67 (d, 3H), 1.75 (d, 3H), 1.86 (d, 3H ), 2.51 (m, 1H), 2.69 (s, 3H), 3.87 (s, 3H), 5.27 (dd, 1H), 5.48 (m, 1H), 6.42 (d, 1H), 7.51 (d, 1H), 7.84 (s, 1H), 8.16 (s, 1H) |
| Wang581.64 | | δ 0.94 (d, 3H), 0.97 (d, 3H) 1.66 (d, 3H), 2.55 (m, 1H), 2.70 (s, 3H), 3.87 (s, 3H), 4.00 , 4.07 (dd, 2H), 4.59 , 4.64 (dd, 2H), 5.26 (dd, 1H), 5.47 (m, 1H), 7.28-7.34 (6H), 7.51 (d, 1H), 7.87 (s, 1H), 8.15 (s, 1H). |
| Wang555.58-L | | δ 1.00 (d, 3H), 1.04 (d, 3H), 1.67 (d, 3H), 2.56 (m, 1H), 2.70 (s, 3H), 3.88 (s, 3H), 5.40 (dd, 1H), 5.47 (m, 1H), 7.07 (d, 1H), 7.20 (dd, 1H), 7.40 (dd, 1H), 7.53~7.60 (3H), 7.88 (s, 1H), 8.71 (s, 1H) |

TABLE 1-11-continued

| Compound | Structure formula | ¹H NMR (CDCl₃, 300 MHz) data |
| --- | --- | --- |
| Wang551.62 | | δ 0.73 (d, 3H), 0.86 (d, 3H), 1.66 (d, 3H), 2.41 (m, 1H), 2.68 (s, 3H), 3.63 (s, 2H), 3.86 (s, 3H), 5.19 (dd, 1H), 5.47 (m, 1H), 6.25 (d, 1H), 7.25-7.36 (5H), 7.52 (d, H), 7.81 (s, 1H), 8.15 (s, 1H) |
| Wang501.56-1 | | δ 0.72-0.81 (m, 4H), 0.94 (d, 3H), 0.96 (d, 3H), 1.48 (m, 1H), 1.67 (d, 3H), 2.45 (m, 1H), 2.69 (s, 3H), 3.87 (s, 3H), 5.24 (dd, 1H), 5.48 (m, 1H), 6.60 (d, 1H), 7.54 (d, 1H), 7.84 (s, 1H), 8.16 (s, 1H) |
| Wang515.58-1 | | δ 0.93 (d, 6H), 1.67 (d, 3H), 1.96 (m, 2H), 2.16-2.32 (4H), 2.44 (1H), 2.69 (s, 3H), 3.09 (m, 1H), 3.88 (s, 3H), 5.22 (dd, 1H), 5.52 (m, 1H), 6.16 (d, 1H), 7.52 (d, 1H), 7.84 (s, 1H), 8.16 (s, 1H) |
| Wang555.58-J | | δ 1.02 (d, 3H), 1.04 (d, 3H), 1.68 (d, 3H), 2.64 (m, 1H), 2.70 (s, 3H), 3.88 (s, 3H), 5.46-5.54 (m, 2H), 7.15 (ddd, 1H), 7.26 (td, 1H), 7.38 (dd, 1H), 7.45-7.51 (m, 1H), 7.52 (d, 1H), 7.87 (s, 1H), 8.06 (td, 1H), 8.17 (s, 1H) |

TABLE 1-11-continued

| Compound | Structure formula | $^1$H NMR (CDCl$_3$, 300 MHz) data |
|---|---|---|
| Wang529.61-1 | | δ 0.94 (d, 3H), 0.95 (d, 3H), 1.55 (m, 3H), 1.68 (d, 3H), 1.72-1.92 (m, 5H), 2.47 (m, 1H), 2.61 (m, 1H), 2.70 (s, 3H), 3.89 (s, 3H), 5.24 (dd, 1H), 5.49 (m, 1H), 6.26 (d, 1H), 7.53 (d, 1H), 7.84 (s, 1H), 8.17 (s, 1H) |
| Wang543.64-1 | | δ 0.93 (d, 3H), 0.95 (d, 3H), 1.26 (m, 4H), 1.50 (m, 2H), 1.68 (d, 3H), 1.77 (m, 2H), 1.88 (m, 2H), 2.20 (m, 1H), 2.47 (m, 1H), 2.70 (s, 3H), 3.88 (s, 3H), 5.24 (dd, 1H), 5.49 (m, 1H), 6.25 (d, 1H), 7.53 (d, 1H), 7.84 (s, 1H), 8.17 (s, 1H) |

Example 12

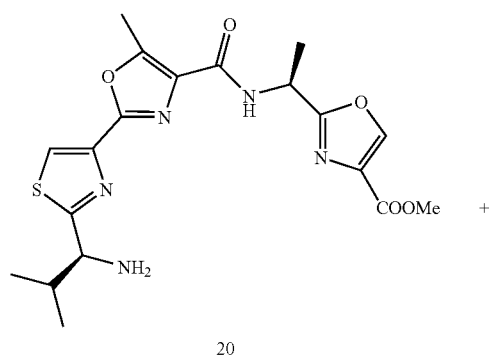

20

NMM, ClCOO$^i$Bu/CH$_2$Cl$_2$

-continued

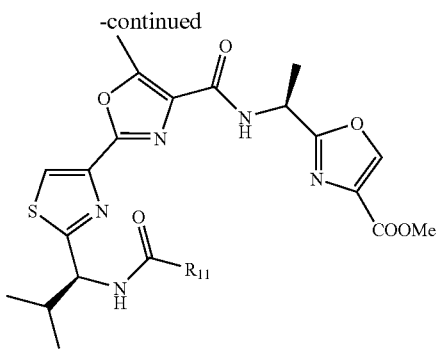

22

Acid (0.06 mmol) was dissolved in CH$_2$Cl$_2$ (5 mL), and cooled in ice salt bath (−18° C.). After 10 minutes, N-methylmorpholine (NMM) (0.075 mmol) and isobutyl chloroformate (ClCOO$^i$Bu) (0.065 mmol) were added thereto in turn. Then stir was proceeded for half an hour, compound 20 (0.05 mmol) was added thereto. Stir was continued, and the system was heated to room temperature gradually. The reaction was tracked by TLC. The reaction was quenched with water after the reaction was completed. The reactant was extracted with EtOAc. The organic phase was washed with saturated salt solution, dried over MgSO$_4$ and concentrated. The mixture was purified through column chromatography (petroleum ether/ethyl acetate (volume ratio 1:1)) to obtain product 22 (Wang529.61-2). The yield was 50%. The following compounds were synthesized by the same method:

TABLE 1-12

| Compound | Structure formula | ¹H NMR (CDCl₃, 300 MHz) data |
|---|---|---|
| Wang529.61-2 | | δ 0.92 (d, 3H), 0.96 (d, 3H), 1.68 (s, 3H), 1.69 (d, 3H), 1.80 (s, 3H), 2.50 (m, 1H), 2.71 (s, 3H), 3.03 (d, 2H), 3.90 (s, 3H), 5.22 (dd, 1H), 5.35 (m, 1H), 5.50 (m, 1H), 6.47 (d, 1H), 7.51 (d, 1H), 7.86 (s, 1H), 8.17 (s, 1H) |
| Wang501.56-2 | | δ 0.94 (d, 3H), 0.95 (d, 3H) 1.68 (d, 3H), 2.47 (m, 1H), 2.70 (s, 3H), 3.08 (ddd, 2H), 3.89 (s, 3H), 5.20-5.28 (3H), 5.49 (m, 1H), 5.96 (m, 1H), 6.42 (d, 1H), 7.52 (d, 1H), 7.88 (s, 1H), 8.17 (s, 1H). |
| Wang515.58-2 | | δ 0.84 (d, 3H), 0.95 (d, 3H), 1.68 (d, 3H), 2.39-2.47 (5H), 2.70 (s, 3H), 3.89 (s, 3H), 4.99 (d, 1H), 5.06 (d, 1H), 5.24 (dd, 1H), 5.49 (m, 1H), 5.81 (m, 1H), 6.35 (d, 1H), 7.52 (d, 1H), 7.85 (s, 1H), 8.16 (s, 1H) |
| Wang543.64-2 | | δ 0.94 (d, 6H), 1.60 (s, 3H), 1.64 (s, 3H), 1.68 (d, 3H) 2.28-2.38 (4H), 2.44 (m, 1H), 2.70 (s, 3H), 3.89 (s, 3H), 5.09 (m, 1H), 5.24 (dd, 1H), 5.49 (m, 1H), 6.31 (d, 1H), 7.51 (d, 1H), 7.85 (s, 1H), 8.16 (s, 1H). |

TABLE 1-12-continued

| Compound | Structure formula | $^1$H NMR (CDCl$_3$, 300 MHz) data |
|---|---|---|
| Wang541.62 | 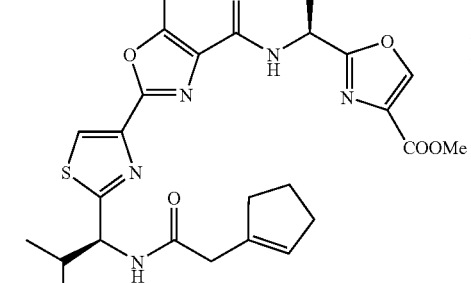 | δ 0.92 (d, 3H), 0.96 (d, 3H), 1.69 (d, 3H), 1.92 (m, 2H), 2.29~2.39 (4H), 2.49 (m, 1H), 2.71 (s, 3H), 3.12 (s, 2H), 3.89 (s, 3H), 5.23 (dd, 1H), 5.56 (m, 1H), 5.65 (m, 1H), 6.46 (d, 1H), 7.50 (d, 1H), 7.86 (s, 1H), 8.17 (s, 1H) |
| Wang555.65 | 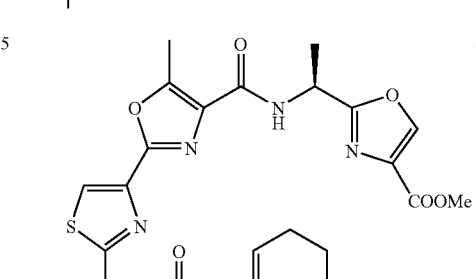 | δ 0.91 (d, 3H), 0.96 (d, 3H), 1.57-1.65 (m, 4H), 1.69 (d, 3H), 1.99 (m, 2H), 2.07 (m, 2H), 2.51 (m, 1H), 2.71 (s, 3H), 2.95 (s, 2H), 3.89 (s, 3H), 5.22 (dd, 1H), 5.51 (dt, 1H), 5.70 (m, 1H), 6.52 (d, 1H), 7.50 (d, 1H), 7.86 (s, 1H), 8.17 (s, 1H) |

Example 13

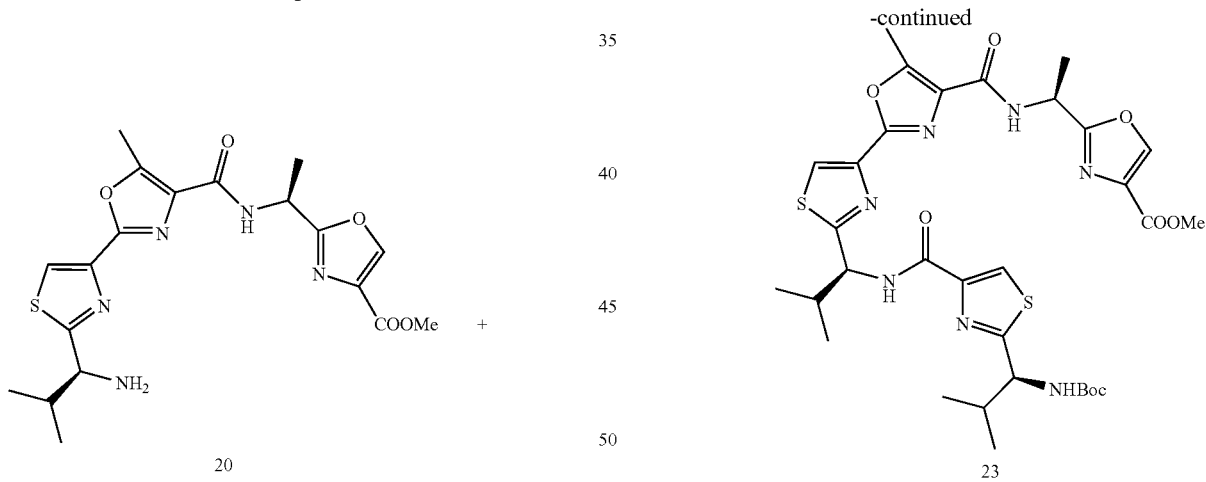

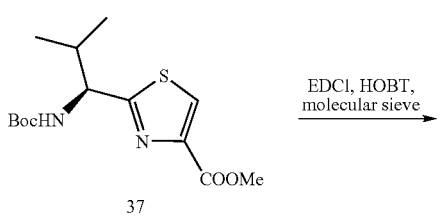

Compound 20 (0.023 mmol) was mixed with a molecular sieve (100 mg) and HOBt (0.023 mmol). The resulted mixture was added 1 mL treated DMF, cooled in ice salt bath (−18° C.) and stirred for 10 minutes. Subsequently, compound 37 (0.023 mmol) was added thereto. After stir was continued for half an hour, N-ethyl-N'-(3-dimethylaminopropyl)carbodiimide (EDCI) (0.025 mmol) was added to the system. The reaction proceeded to react for half an our in ice salt bath, and the system was heated to room temperature gradually. After the reaction was completed, the system was diluted with EtOAc. The organic phase was washed with water and saturated NaCl solution 3 times respectively, dried over MgSO$_4$, and the solvent was concentrated. The mixture was purified through column chromatography (petroleum ether/ethyl acetate (volume ratio 1:1)) to obtain product 23 (Wang715.84). The yield was 97%. The following compounds were synthesized by the same method:

TABLE 1-13

| Compound | Structure formula | $^1$H NMR (CDCl$_3$, 300 MHz) data |
| --- | --- | --- |
| Wang715.84 | | δ 0.93 (d, 3H), 1.00 (d, 3H), 1.03 (d, 3H), 1.04 (d, 3H), 1.44 (s, 9H), 1.70 (d, 3H), 2.38 (m, 1H), 2.72 (s, 3H), 3.90 (s, 3H), 4.90 (m, 1H), 5.14 (d, 1H), 5.37 (dd, 1H), 5.50 (m, 1H), 7.52 (d, 1H), 7.88 (s, 1H), 7.90 (d, 1H), 8.03 (s, 1H), 8.18 (s, 1H) |
| Wang653.71 | | δ 1.04 (d, 3H), 1.06 (d, 3H), 1.50 (s, 9H), 1.70 (d, 3H), 2.67-2.72 (m, 1H), 2.72 (s, 3H), 3.90 (s, 3H), 5.39 (dd, 1H), 5.51 (m, 1H), 7.42 (dd, 1H), 7.53 (d, 1H), 7.81 (s, 1H), 8.18 (dd, 1H), 8.86 (dd, 1H), 9.08 (d, 1H), 11.01 (s, 1H). |
| Wang538.58 | | δ 1.04 (d, 3H), 1.05 (d, 3H), 1.70 (d, 3H), 2.71 (s, 3H), 2.68-2.74 (m, 1H), 3.89 (s, 3H), 5.45 (dd, 1H), 5.50 (m, 1H), 7.47 (ddd, 1H), 7.55 (d, 1H), 7.86 (s, 1H), 7.87 (td, 1H), 8.17 (s, 1H), 8.20 (dd, 1H), 8.60 (ddd, 1H), 8.76 (d, 1H) |

Example 14

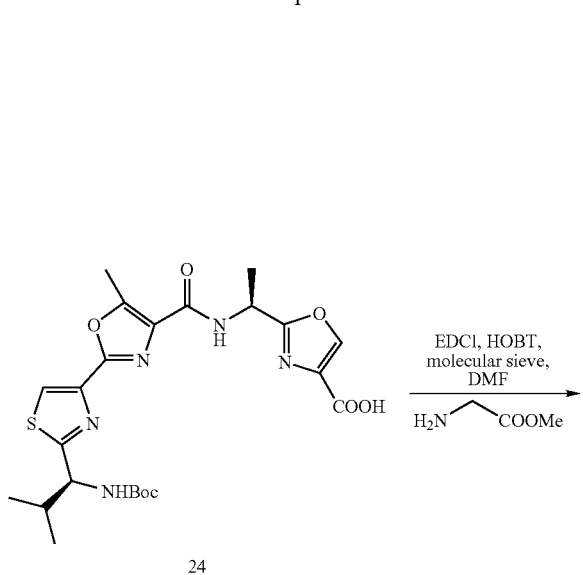

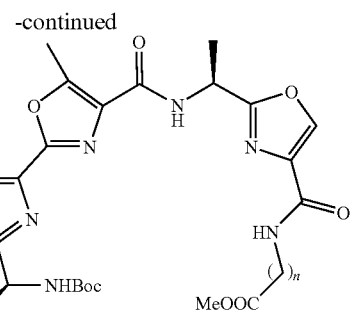

Compound 24 (0.023 mmol) was mixed with a molecular sieve (100 mg) and HOBt (0.023 mmol). The resulted mixture was added 1 mL treated DMF, cooled in ice salt bath (−18° C.) and stirred for 10 minutes. Subsequently, glycine methane ester (0.023 mmol) was added thereto. After stir was continued for half an hour, N-ethyl-N'-(3-dimethylaminopropyl) carbodiimide (EDCI) (0.025 mmol) was added to the system. The reaction proceeded to react for half an hour in ice salt bath, then the system was heated to room temperature gradually. After the reaction was completed, the system was diluted with EtOAc. The organic phase was washed with water and saturated NaCl solution 3 times respectively, dried over $MgSO_4$, and the solvent was concentrated. The mixture was purified through column chromatography (petroleum ether/ ethyl acetate (volume ratio 1:1)) to obtain product 25 (Wang715.84). The following compounds were synthesized by the same method:

TABLE 1-14

| Compound | Structure formula | $^1$H NMR (CDCl$_3$, 300 MHz) data |
|---|---|---|
| Wang590.22 | | δ 0.90 (d, 3H), 1.00 (d, 3H), 1.44 (s, 9H), 1.66 (d, 3H), 2.49 (m, 1H), 2.71 (s, 3H), 3.76 (s, 3 h), 4.18 (d, 2H), 4.49 (m, 1H), 5.26 (m, 1H), 5.45 (m, 1H), 7.45 (br, 1H), 7.57 (d, 1H), 7.87 (s, 1H), 8.14 (s, 1H). |
| Wang604.23 | | δ 0.87 (d, 3H), 0.96 (d, 3H), 1.39 (s, 9H), 1.60 (d, 3H), 2.46 (m, 1H), 2.58 (t, 2H), 2.66 (s, 3H), 3.61 (t, 3H), 3.64 (s, 3H), 4.90 (m, 1H), 5.34 (m, 1H), 5.41 (m, 1H), 7.41 (m, 1H), 7.56 (d, 1H), 7.84 (s, 1H), 8.08 (s, 1H) |

TABLE 1-14-continued

| Compound | Structure formula | ¹H NMR (CDCl₃, 300 MHz) data |
|---|---|---|
| Wang646.28 | | δ 0.90 (d, 3H), 0.99 (d, 3H), 1.43 (s, 9H), 1.59~1.69 (m, 6H), 1.63 (d, 3H), 2.29 (t, 2H), 2.48 (m, 1H), 2.70 (s, 3H), 3.37 (m, 2H), 3.63 (s, 3H), 4.95 (m, 1H), 5.27 (m, 1H), 5.44 (m, 1H), 7.01 (m, 1H), 7.53 (d, 1H), 7.84 (s, 1H), 8.10 (s, 1H) |
| Wang632.26 | | δ 0.86 (d, 3H), 0.95 (d, 3H), 1.39 (s, 9H), 1.59 (d, 3H), 1.55-1.65 (m, 4H), 2.29 (t, 2H), 2.43 (m, 1H), 2.65 (s, 3H), 3.51 (m, 2H), 3.59 (s, 3H), 4.90 (m, 1H), 5.33 (d, 1H), 5.39 (m, 1H), 7.09 (br, 1H), 7.57 (d, 1H), 7.81 (s, 1H), 8.08 (s, 1H). |
| Wang618.25 | | δ 0.87 (d, 3H), 0.96 (d, 3H), 1.40 (s, 9H), 1.60 (d, 3H), 1.87 (m, 2H), 2.32 (t, 2H), 2.44 (m, 1H), 2.66 (s, 3H), 3.41 (m, 2H), 3.61 (s, 3H), 4.91 (m, 1H), 5.30 (m, 1H), 5.40 (m, 1H), 7.11 (br, m), 7.54 (d, 1H), 7.82 (s, 1H), 8.08 (s, 1H). |

Example 15

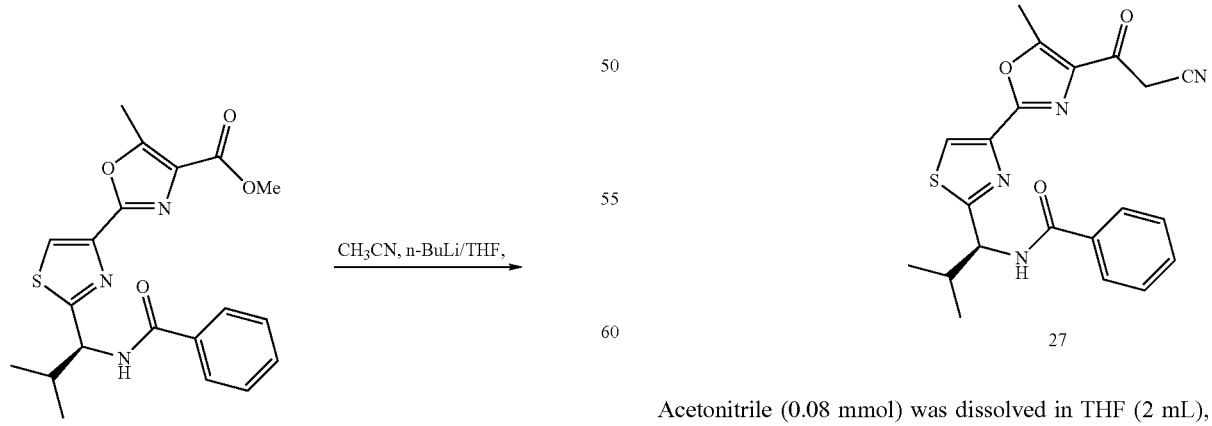

Acetonitrile (0.08 mmol) was dissolved in THF (2 mL), cooled at −78° C. and added butyllithium (0.1 mmol). The reaction was conducted for 10 minutes. Compound 26 (0.08 mmol) was added to the system, and reaction was conducted at −78° C. The reaction was quenched with saturated NH₄Cl after an hour. The reactant was extracted with EtOAc, dried over MgSO$_4$ and concentrated. The mixture was purified through column chromatography (petroleum ether/ethyl acetate (volume ratio 1:1)) to obtain product 27. The yield was 56%. $^1$H NMR (CDCl$_3$, 300 MHz) δ 1.04 (d, 3H), 1.07 (d, 3H), 2.58 (m, 1H), 2.74 (s, 3H), 4.18 (s, 2H), 5.47 (dd, 1H), 6.93 (d, 1H), 7.44-7.55 (3H), 7.83-7.86 (2H), 7.94 (s, 1H).

Example 16

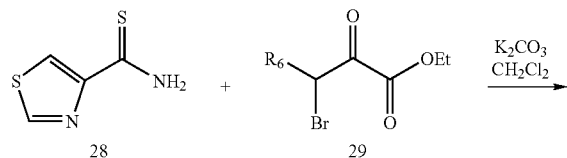

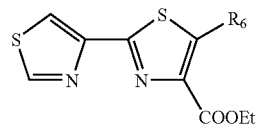

Compound 28 (1 eq) was mixed with K$_2$CO$_3$ (10 eq). The resulted mixture was dissolved in 50 mL CH$_2$Cl$_2$, and compound 29 (1.1 eq) was added thereto. The progress of reaction was tracked by TLC. The reaction solution was concentrated, then purified through column chromatography (petroleum ether/ethyl acetate (volume ratio 5:1)) to obtain product 30 (yield 60%). The following compounds were obtained by the same method:

TABLE 1-15

| Compound | Structure formula | $^1$H NMR (CDCl$_3$, 300 MHz) data |
|---|---|---|
| Wang240 | | δ 1.41 (t, 3H), 4.43 (q, 2H), 8.18 (s, 1H), 8.23 (s, 1H), 8.85 (s, 1H). |
| Wang254 | | δ 1.3 (t, 3H), 2.78 (s, 3H), 4.34 (q, 2H), 8.20 (s, 1H), 8.85 (s, 1H). |

Example 17

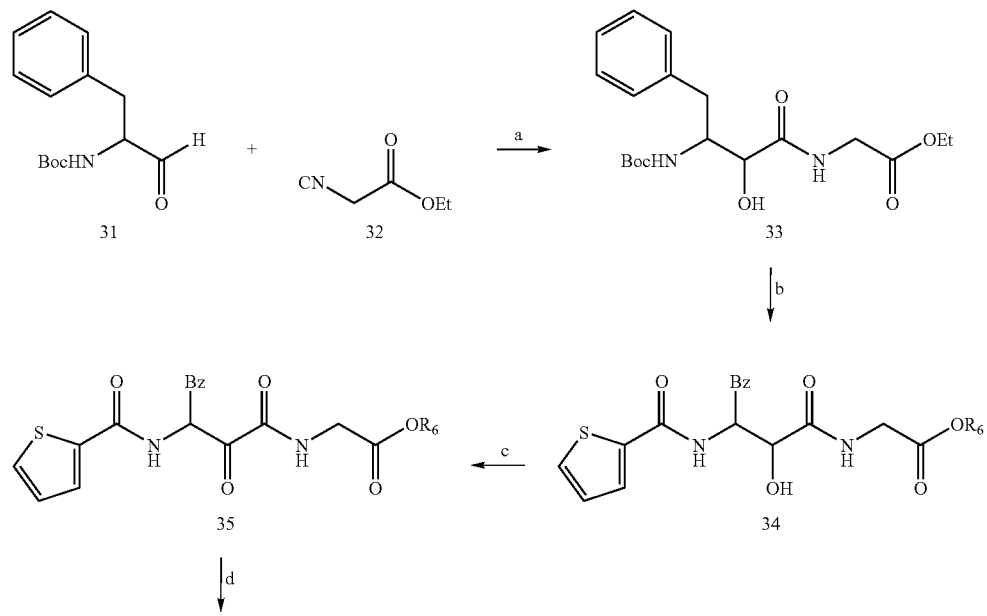

-continued

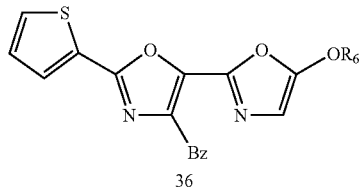
36 a TFA(trifluoroacetic acid), pyridine, CH₂Cl₂;
b 4N HCl/dioxane, thiophine-2-formic acid, EDCI, DMAP, DMF;
c IBX, toluene/DMSO;
d POCl₃

Compound 31 (1.24 g), compound 32 (0.82 mL), pyridine (1.61 mL) and 100 mL CH₂Cl₂ were mixed, then TFA (0.75 mL) was added thereto at −10° C. The reaction was conducted for 2 hours while maintaining this temperature, then the system was heated to room temperature to react. The progress of reaction was tracked by TLC. The reaction solution was concentrated and dissolved in 150 mL EtOAc, water was added thereto, then acidified with 1N hydrochloric acid (30 mL). The EtOAc phase was separated. The organic phase was washed 3 times with 50 mL saturated NaCl solution, dried over MgSO₄, and the organic phase was concentrated. The mixture was purified through column chromatography (petroleum ether/ethyl acetate (volume ratio 3:1)) to obtain compound 33 (1.25 g, yield 66%). Compound 33 (650 mg) was mixed with solution (7 mL) of 4N dioxane in hydrogen chloride at 0°. The progress of reaction was tracked by TLC. After the reaction was completed, the reaction solution was concentrated to obtain the intermediate. The intermediate was mixed with thiophene-2-fromic acid (241 mg), EDCI (392 mg), DMAP (42 mg) and pyridine (0.3 mL), DMF (7 mL) was added thereto. The reaction was conducted at room temperature, and tracked by TLC. After the reaction was completed, the system was diluted with 100 mL EtOAc. The organic phase was washed 3 times with 100 mL water and 50 mL saturated NaCl solution respectively, dried over MgSO₄, and the organic phase was concentrated. The mixture was purified through column chromatography (petroleum ether/ethyl acetate (volume ratio 1:1)) to obtain compound 34 (220 mg). Compound 34 (90 mg) was mixed with IBX (77.5 mg), the mixed solvent of toluene/DMSO (1 mL/0.5 mL) was added thereto. The reaction was conducted for 2 hours at 50°, the solid was removed by vacuum filtration. The filtrate was diluted with 100 mL ethyl ether, washed 3 times with 50 mL saturated NaHCO₃ solution, dried over MgSO₄. The organic phase was concentrated to obtain compound 35 (80 mg). Compound 35 (25 mg) was mixed with POCl₃ (0.5 mL) and heated to 80°. The progress of reaction was tracked by TLC. Subsequently the reaction solution was poured into 50 mL saturated sodium bicarbonate (NaHCO₃) solution of 0°. POCl₃ was removed. Then the reactant was extracted with 50 mL ethyl acetate, washed 3 times with 50 mL saturated NaCl solution, dried over MgSO₄, and the organic phase was concentrated. The mixture was purified through column chromatography (petroleum ether/ethyl acetate (volume ratio 2:1)) to obtain product, compound 36 (8 mg).

TABLE 1-16

| Compound | Structure formula | ¹H NMR (CDCl₃, 300 MHz) data |
|---|---|---|
| C352 | (structure) | δ 1.47 (t, 3H), 4.20 (q, 2H), 4.26 (s, 1H), 6.28 (s, 1H), 7.11 (dd, 1H), 7.23 (dd, 1H), 7.27~7.31 (m, 2H), 7.38~7.41 (m, 2H), 7.45 (d, 1H), 7.77 (d, 1H) |

Example 18

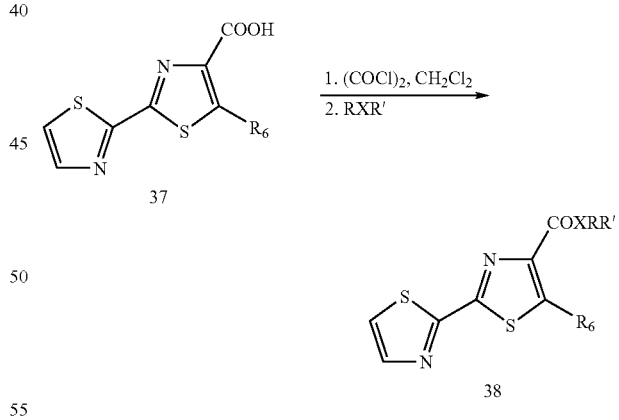

Compound 37 (1 mmol) was dissolved in dichlomethane, 1.2 Eq oxalyl chloride was added thereto. The resulted mixture was stirred overnight at room temperature. After the reaction solution was rotary dried, dichlomethane was added thereto, then 1.5 Eq aminobenzene was added. After the resulted mixture was stirred for several hours at room temperature, water was added thereto, extracted 2 times with dichlomethane. The organic phase was washed 2 times with 1N hydrochloric acid and 1 times with saturated salt water, dried over MgSO₄, and the organic phase was concentrated. The mixture was purified through column chromatography to obtain product 38 (C343). The following compounds were synthesized by the same method:

Under action of antiviral drugs, the contents of HBsAg, HBeAg and viral DNA secreted from cells into the superna-

TABLE 1-17

| Compound | Structure formula | $^1$H NMR (CDCl$_3$, 300 MHz) data |
| --- | --- | --- |
| C357 | [structure: bithiazole with isobutyl and CONHCH$_2$Ph] | 1.02 (d, J = 6.6 Hz, 6H), 2.04 (m, 1H), 3.31 (d, J = 7.2 Hz, 2H), 4.64 (d, J = 6.3 Hz, 2H), 7.34 (bm, 5H), 7.85 (d, J = 3.3 Hz, 2H). |
| C267 | [structure: bithiazole with isobutyl and CONH$_2$] | 1.01 (d, J = 6.6 Hz, 6H), 2.02 (m, 1H), 3.28 (d, J = 6.9 Hz, 2H), 5.60 (bs, 2H), 7.43 (d, J = 3.0 Hz, 1H), 7.88 (d, J = 3.0 Hz, 1H). |
| C343 | [structure: bithiazole with isobutyl and CONHPh] | 1.02 (d, J = 6.6 Hz, 6H), 2.04 (m, 1H), 3.31 (d, J = 7.2 Hz, 2H), 4.64 (d, J = 6.3 Hz, 2H), 7.34 (bm, 4H), 7.85 (d, J = 3.3 Hz, 1H). |
| C295-3 | [structure: bithiazole with isobutyl and CON(CH$_3$)$_2$] | 0.93 (d, J = 6.6 Hz, 6H), 1.90 (m, 1H), 2.84 (d, J = 6.9 Hz, 2H), 3.02 (s, 3H), 3.09 (s, 3H), 7.39 (d, J = 3.3 Hz, 1H), 7.82 (d, J = 3.0 Hz, 1H). |
| C281 | [structure: bithiazole with isobutyl and CONHMe] | 0.98 (d, J = 6.6 Hz, 6H), 1.99 (m, 1H), 2.98 (d, J = 4.8 Hz, 3H), 3.26 (d, J = 7.2 Hz, 2H), 7.42 (d, J = 3.3 Hz, 1H), 7.44 (bs, 1 h), 7.85 (d, J = 3.3 Hz, 1H). |
| C310-4 | [structure: bithiazole with isobutyl and COO-iPr] | 1.00 (d, 6H), 1.42 (d, 6H), 2.00 (m, 1H), 3.12 (d, 3H), 5.29 (m, 1H), 7.45 (d, 1H), 7.86 (d, 1H). |

Experimental Example

Experimental Example 1

Anti Hepatitis B Virus (HBV) Activity Test

1. Object of the Experiment:

The synthetic compounds of the present invention are screened for their anti hepatitis B virus (HBV) activity. The experiment includes testing the cytotoxicity of the test compounds, and the effect of the test compounds on secretion of surface antigen and core antigen of hepatitis B virus and on replication level of virus nucleic acid (DNA) in a virus-cell level experiment.

2. Principle of the Experiment:

Hepatitis B virus (HBV) transgenic human hepatoma carcinoma cell, HepG2.2.15 cell line, can secrete hepatitis B virus particles (containing antigen and DNA) into supernatant when being cultured.

tant were detected and are compared with the contents of control groups without drugs, so that the antiviral activity of the compounds of the present invention can be measured as well as the cytotoxic effect of compounds of the present invention. The value concentration of the compounds of the present invention which caused 50% of cells dead and was measured with MTT method was CC$_{50}$; and the value concentration of the compounds of the present invention which inhibited the secretion of HBsAg and HBeAg detected by ELISA method and inhibited 50% of viral DNA replication detected by fluorescent quantification PCR method was IC$_{50}$.

3. Samples:

The solutions of the test compounds was prepared before use. Each compound was tested with 7 dilution concentrations, and the antiviral drugs, such as lamivudine etc. were used as positive control drugs to check if the experimental reaction is normal or not each time.

4. Method:

a) Experimental Process and Collection of Culture Supernatant

HepG2.2.15 cells were inoculated on a 96-well plate, and the compounds of the present invention were added next day. The medium and the compound solutions of the same concentration were renewed periodically. The culture supernatants were collected on the eighth day to be detected. MTT was added to the cells on the 96-well plate, and MTT dissolving liquid was added after 4 hours to be reacted overnight. $OD_{570}$ was measured next day on microplate reader. And the cytotoxicity of the compounds of the present invention to the HepG2.2.15 cells, the effect of the compounds of the present invention on the growth of the cells, and the concentration of the compound of the present invention ($CC_{50}$) causing 50% of the cells dead were estimated according to the OD values.

b) Detection of the Contents of HBsAg and HBeAg in Culture Supernatant (ELISA Method):

HBsAg and HBeAg were detected with assaying kits (purchased from Sino-American biotechnological company). Samples were added to the coated strip plate, and the same amount of enzyme labeled conjugate was added, after reacting under 37° C. for 1 hour, the plate was washed 5 times. Colorant solutions A and B were added, and the reaction was stopped after 15 minutes, and $OD_{450/630}$ was measured. The half inhibition rate $IC_{50}$ of the sample for the HBV antigen was calculated according to the OD values.

c) Detection of the Content of HBV-DNA in Culture Supernatant by Fluorescent Quantification PCR:

A suitable amount of culture supernatant was added into a same volume of virus extract solution, and was boiled after mixed uniformly, then centrifuged at 10000 rpm for 5 min under room temperature. A suitable amount of supernatant was collected for PCR amplification. Five HBV-DNA standard samples were used to set a standard curve. According to the obtained viral DNA replication value, the inhibition rates of HBV-DNA replication of the compound of the present invention at different concentrations were calculated, and then the half inhibition rates of the compounds were calculated to obtain $IC_{50}$. For the samples that can not be calculated for $IC_{50}$ value, they can be represented by $IC_X$ and given the corresponding concentration values.

The PCR primers used in the experiment are:

P1:     5'ATCCTGCTGCTATGCCTCATCTT3'

P2:     5'ACAGTGGGGAAAGCCCTACGAA3'

The PCR probes used in the experiment are:

5'TGGCTAGTTTACTAGTGCCATTTTG3'

5. Experimental Results:

TABLE 2-1

| Sample No. | Cytotoxicity $CC_{50}$ (uM) | HBsAg secreation $IC_{50}$ (SI) (uM) | HBeAg secreation $IC_{50}$ (SI) (uM) | DNA replication $IC_{50}/IC_X$ (SI) (uM) |
|---|---|---|---|---|
| Wang338 | 200.3 | 77.6 (2.58) | 22.3 (9) | 6.1 (32.8) |
| Wang278 | 152.7 | 67.35 (2.27) | 24 (6.4) | 4.8 (32.1) |
| Wang282-1 | >333 | 67.57 (>4.93) | 21.67 (>15.4) | 2.4 (>138.8) |
| Wang282 | 396.9 | 58.8 (6.75) | 57.3 (6.9) | 19.4 (20.5) |
| Wang278-1 | 90.3 | 34.1 (2.6) | 19 (4.8) | $IC_{88}$ = 1.37 |
| Wang405.49 | 154.1 | 63.5 (2.43) | 46 (3.32) | 76 (2.02) |
| C227 | >100 | NT | NT | 1.4 (>71) |
| C306 | >100 | NT | NT | 0.8 (>125) |
| C310 | >100 | NT | NT | 0.14 (>571) |
| C324-2 | >100 | NT | NT | 0.14 (>571) |
| C311-2 | 3.5 | NT | NT | 0.07 (50) |
| C325-2 | 5.6 | NT | NT | NC |
| C328-2 | 21.7 | NT | NT | NC |
| C376 | 126.6 | NT | NT | 23 (6) |
| C296-3 | 115.7 | NT | NT | 0.14 (826) |
| C226 | 53.2 | NT | NT | 2.3 (23.1) |
| C243 | 84.5 | NT | NT | 0.41 (206.1) |
| C262 | 34.4 | NT | NT | 4.3 (8) |
| C263-1 | >100 | NT | NT | 3.7 (>27) |
| C277 | >100 | NT | NT | 3.1 (>32) |
| C291 | >100 | NT | NT | 5.5 (>18.2) |
| C304 | >100 | NT | NT | 4.5 (>22.2) |
| C305-1 | >100 | NT | NT | 2.6 (>38) |
| C305-2 | >100 | NT | NT | 4.1 (>24.4) |
| C321-2 | 28.2 | NT | NT | 1.67 (>16.9) |
| C324 | 61 | NT | NT | NC |
| C267 | >100 | NT | NT | $IC_{89}$ = 33 |
| C279-3 | >100 | NT | NT | NC |
| C280-1 | >100 | NT | NT | NC |
| C279-2 | 71.8 | NT | NT | 51.9 (1.38) |
| C279-1 | 94.69 | NT | NT | $IC_{40}$ = 12.4 |
| C208 | >100 | NT | NT | 35.8 (>2.8) |
| C280-2 | >100 | NT | NT | $IC_{26}$ = 0.41 |
| C281 | >100 | NT | NT | $IC_{94}$ = 33 |
| C292 | 138.9 | NT | NT | 4.65 (25.9) |
| C293 | 80 | NT | NT | 126.2 (0.6) |
| C295-1 | 50 | NT | NT | 11.7 (4.3) |
| C295-3 | >100 | NT | NT | $IC_{12}$ = 1.23 |
| C296-2 | >100 | NT | NT | $IC_{12}$ = 0.41 |

TABLE 2-1-continued

| Sample No. | Cytotoxicity $CC_{50}$ (uM) | HBsAg secreation $IC_{50}$ (SI) (uM) | HBeAg secretion $IC_{50}$ (SI) (uM) | DNA replication $IC_{50}/IC_X$ (SI) (uM) |
|---|---|---|---|---|
| C307 | 80 | NT | NT | 22.5 (3.6) |
| C309 | >100 | NT | NT | $IC_{14.2}$ = 0.39 |
| C321-1 | 80 | NT | NT | 5.86 (13.65) |
| C321-3 | 80 | NT | NT | $IC_{27}$ = 1.23 |
| C328 | >7.5 | NT | NT | 0.19 (>39.14) |
| C329 | >100 | NT | NT | $IC_{41.8}$ = 4 |
| C337 | 60 | NT | NT | NC |
| C343 | 50 | NT | NT | $IC_{19}$ = 1.23 |
| C345 | >88.1 | NT | NT | 1.32 (>86.7) |
| C352 | >33.3 | NT | NT | 8.3 (>4) |
| C357 | 80 | NT | NT | $IC_{89}$ = 33 |

TABLE 2-2

| Sample No. | Cytotoxicity $CC_{50}$ (uM) | HBsAg secretion $IC_{50}$ (SI) (uM) | HBeAg secreation $IC_{50}$ (SI) (uM) | DNA replication $IC_{50}/IC_X$ (SI) (uM) |
|---|---|---|---|---|
| Wang279-1 | 785.7 | 142.6 (5.5) | 102.1 (7.7) | $IC_{60}$ = 37 |
| Wang265 | 548.5 | 130.8 (4.2) | 38.8 (14.1) | $IC_{44}$ = 4.1 |
| Wang240 | 611.4 | 63.9 (9.6) | 182.1 (3.4) | $IC_{34}$ = 31.3 |
| Wang260 | 269.7 | 71.4 (3.8) | 130 (3.1) | $IC_{85}$ = 37 |
| Wang268 | 256.7 | 37.2 (6.9) | 127.7 (2) | $IC_{53}$ = 125 |
| Wang268-1 | 437.3 | 90 (4.9) | 100.7 (4.3) | 153.1 (2.9) |
| Wang298 | 568.6 | 143.5 (4) | 209.4 (2.7) | NC |
| Wang316 | 173.6 | 33.7 (5.2) | 70.5 (2.5) | $IC_{20}$ = 31.3 |

TABLE 2-3

| Sample NO. | Cytotoxicity $CC_{50}$ (uM) | HBsAg secreation $IC_{50}$ (SI) (uM) | HBeAg secretion $IC_{50}$ (SI) (uM) | DNA replication $IC_{50}/IC_X$ (SI) (uM) |
|---|---|---|---|---|
| Wang261 | 123.3 | 92.4 (1.3) | 37 (3.3) | NC |
| Wang264 | 124.5 | 41.3 (3) | 95.5 (1.3) | NC |
| Wang302 | 192.2 | NC | 83.2 (2.3) | 63.1 (3.1) |
| Wang294 | >1000 | >1000 | 1139 (>0.88) | $IC_{60}$ = 37 |
| Wang417.46-J | 754.6 | 143.0 (5.3) | NC | NC |
| Wang529.61-1 | 472.04 | 214 (2.21) | 171.1 (2.76) | NC |

Note:
$CC_{50}$ indicates the effect of the compounds of the present invention on the growth of HepG2.2.15 cell, 50% death concentration.
$IC_{50}$ is the concentration of the compounds of the present invention that inhibits 50% of the antigen or DNA replication.
SI is the selection coefficient of biological activity of the compounds of the present invention.
SI value > 2 is effective, and the bigger, the better.
NC indicates no obvious biological activity or non-calculated.
NT means not tested.

Experimental Example 2

The Activity Test of Anti Influenza Virus, Herpes Virus, HIV-1 Revertase, HIV Integrase Biological Activity Test:

1. Screening of the compounds for the anti HIV-1 revertase activity: The template reacted with HIV-1 revertase was coated on the plate, and in the optimized enzyme reaction condition and reaction system, HIV-1 RT may add the substrate containing Biotin-dUTP to the reaction template. The incorporation amount of Biotin-dUTP in the enzyme reaction resultant was detected by streptavidin labeled horse radish peroxidase to reflect the enzyme activity. Addition of the compounds of the present invention in the reaction system can be used to screen the inhibitor of the enzyme.

2. Screening of the compounds for the anti HIV-1 integrase activity: the synthesized 30 oligonucleotide (5'P-ACC CTT TTA GTC AGT GTG GAA AAT CTC TAG CAGT-3',3'-GAA AAT CAG TCA CAC CTT TTA GAG ATC GTCA-5') was used as donor substrate, and the synthesized 20 oligonucleoside (5'-TGA CCA AGG GCT AAT TCA CT-3'-biotin, biotin-3'-ACT GGT TCC CGA TTA AGT GA-5') was used as target substrate. On a 96-well plate, the donor substrate was added with purified HIV-1 integrase to conduct ELISA reaction. The product of chain transfer of target DNA was detected and stained in the biotin labeled alkaline phosphatase system, OD values were measured with microplate reader. Addition of the compounds of the present invention in the reaction system can be used to screen the inhibitor of the enzyme.

3. Screening of the compounds for the anti-herpes virus I and II activity: Vero (African green monkey kidney) cells were used as virus host to test the inhibition effect of the compounds of the present invention on the cytopathic effect of the Vero cells caused by Herpes virus I and II.

4. Screening of the samples for the anti-influenza virus A and B activity: MDCK (canine kidney) cells were used as the virus host to test the inhibition effect of the compounds of the present invention on the cytopathic effect (CPE) of the cells caused by the virus.

Part of the test results of the compounds: $IC_{50}$, $TC_{50}$ (unit: μg/ml).

TABLE 3-1

| No. | $TC_{50}$ | Anti herpes virus I HSV-I ($IC_{50}$) (SI) | Anti herpes virus II HSV-II ($IC_{50}$) (SI) |
|---|---|---|---|
| Wang363.43-1 | 707.11 | 369.21 (1.92) | — |
| Wang417.46-P | 198.43 | — | 106.52 (1.86) |
| Wang 443.52 | 168.24 | 106.52 (1.52) | 78.75 ((1.86) |
| Wang 577.72 | 176.78 | — | 97.59 (1.81) |
| Wang 529.61-1 | 198.43 | — | 106.52 |
| Wang 501.56-1 | 707.11 | — | 293.37 (2.41) |
| ACV (acyclovir) | >1000 | 12.92 (>77.39) | 10.58 (>94.51) |

Note:
(1) "—" in the table represents that there is no anti herpes virus activity when the sample is at the maximal nontoxic dose.
(2) $TC_{50}$: 50% toxity concentration; $IC_{50}$: 50% inhibitory concentration of the virus; SI = $TC_{50}/IC_{50}$.

TABLE 3-2

| Compounds | TC$_{50}$ | Anti influenza A virus (IC$_{50}$) | Compounds | TC$_{50}$ | Anti influenza A virus (IC$_{50}$) |
|---|---|---|---|---|---|
| Wang363.43-1 | 500 | 3.97 | Yao379.47 | 577.35 | 97.81 |
| Wang391.49-1 | 250 | 0.56 | Wang391.49-2 | >1000 | >192.45 |
| Wang417.46-P | 422.43 | 0.90 | Wang 377.46-1 | 500 | 111.11 |
| Wang 399.46 | 166.67 | 1.14 | Wang 417.46-J | >1000 | >86.23 |
| Wang 363.43-2 | 500 | 0.42 | Wang 377.46-2 | 577.35 | 258.69 |
| Wang 443.52 | 165.86 | 1.29 | Wang 501.56-2 | 577.35 | 68.71 |
| Wang 529.61-1 | 191.74 | 3.15 | Wang 555.65 | 577.35 | 44.48 |
| Wang 551.62 | 303.69 | 1.18 | Wang 417.52 | 231.12 | 68.71 |
| Wang 501.56-1 | 303.69 | 1.18 | Wang429.49 | 333.33 | 47.72 |
| Wang 537.59 | >1000 | 1.29 | Wang529.61-2 | 577.35 | 111.11 |
| Wang 403.50 | 333.33 | 64.15 | Wang489.55 | 577.35 | 160.25 |
| Yao 351.42 | 577.35 | 258.68 | Wang 543.64-1 | 144.34 | 57.78 |
| Yao405.51 | 577.35 | 37.03 | Wang389.47 | 480.75 | 29.01 |
| Wang415.46 | 333.33 | 29.01 | Ribavirin | >2000 | 3.73 |

Note:
TC$_{50}$: 50% toxity concentration;
IC$_{50}$: 50% inhibitory concentration of the virus;
SI = TC$_{50}$/IC$_{50}$.

TABLE 3-3

| NO. | HIV-1protease (IC$_{50}$) | HIV-1integrase (IC$_{50}$) |
|---|---|---|
| Wang 399.46 | — | 145.8 |
| Wang 577.72 | 33.3 | — |
| Positive control | 90.1 (nelfinavir) | 0.48 (ABPS-y) |

Note:
(1) "—" represents that the samples have no inhibition of the HIV-1 protease and the HIV-1integrase at the initial concentration. Nelfinaivir and Achyrnthes bidentata polysaccharides (ABPS-y) are positive control drugs for measurement of the inhibition activity of the HIV-1 protease and HIV integrase respectively.

The invention claimed is:

1. A compound having a structure represented by the following structural formula:

wherein,
R2 is hydrogen; C1-C6 alkyl; amido; C1-C4 alkoxycarbonyl; or carboxyl;
R3 and R6 independently are hydrogen; C1-C13 alkyl; halogenated phenyl; benzyl or halogenated benzyl; C1-C6 alkyl substituted by C1-C6 alkoxyl; or C3-C6 cycloalkyl; R7 is hydrogen, C1-C13 alkyl, or amido.

2. The compound according to claim 1, wherein,
R2 is H or C1-C6 alkyl;
R3 is H or C1-C4 alkyl;
R6 is hydrogen, C1-C13 alkyl, C1-C6 alkyl substituted by C1-C6 alkoxyl, or C3-C6 cycloalkyl.

3. A compound selected from the group consisting of:

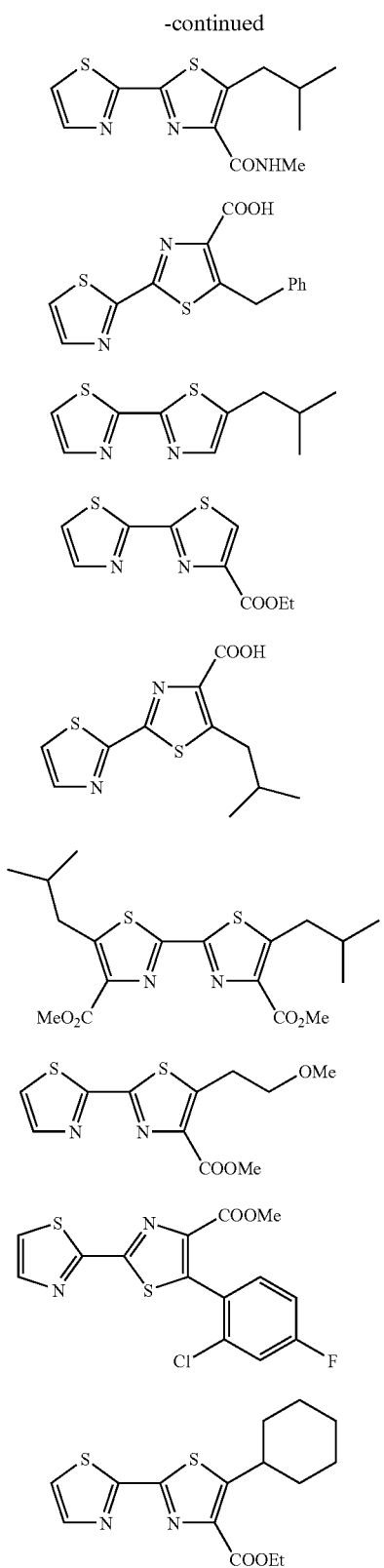
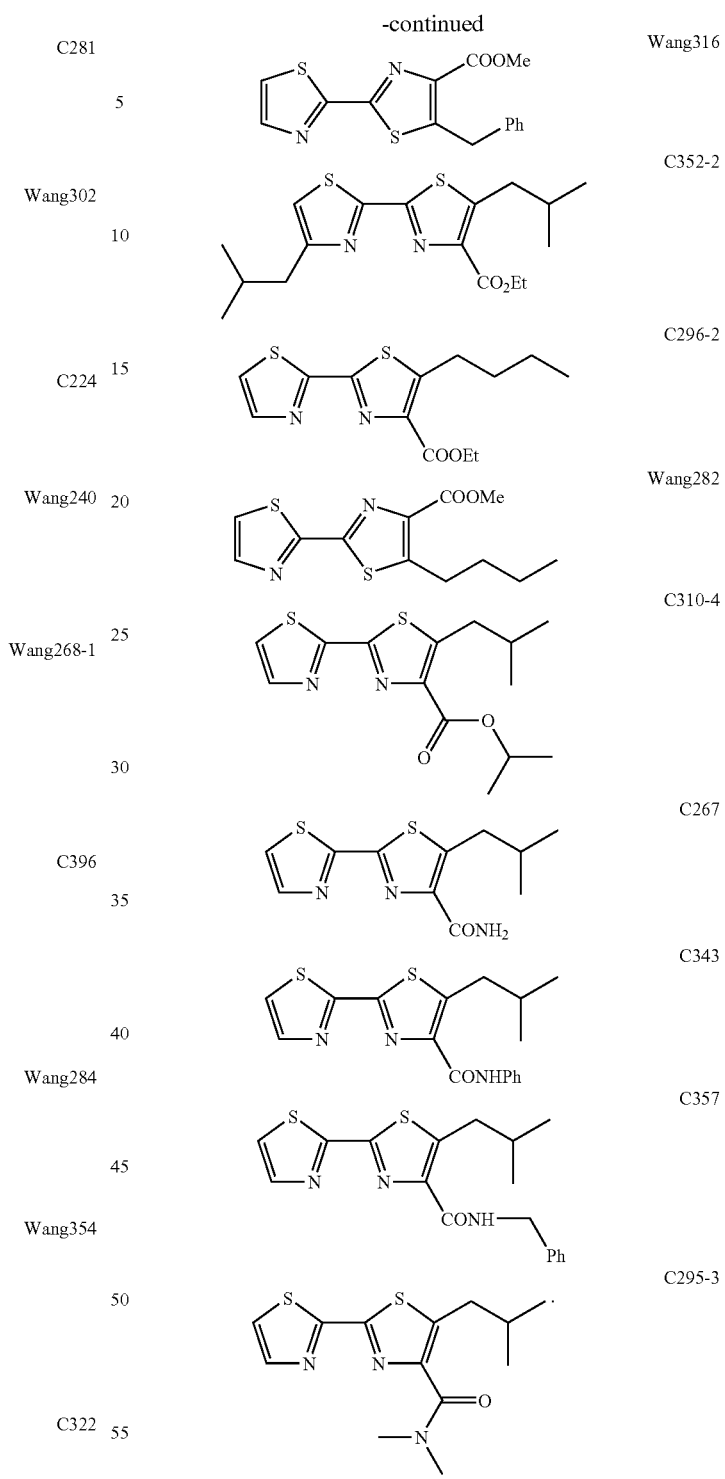
4. A method of treatment comprising administering the compound of claim 1 to a patient for treating HBV, HIV-1, herpes virus 1, herpes virus 2 or influenza virus.
* * * * *